(12) United States Patent
Hayashi et al.

(10) Patent No.: US 12,302,903 B2
(45) Date of Patent: May 20, 2025

(54) OXAZEPINONE DERIVATIVE, AGRICULTURAL/HORTICULTURAL INSECTICIDE CONTAINING THE SAME, AND METHOD FOR USING THE SAME

(71) Applicant: NIHON NOHYAKU CO., LTD., Tokyo (JP)

(72) Inventors: Nobuyuki Hayashi, Kawachinagano (JP); Yoshinori Gosho, Kawachinagano (JP); Masataka Aoshima, Kawachinagano (JP); Hiroko Sato, Kawachinagano (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 773 days.

(21) Appl. No.: 17/631,348

(22) PCT Filed: Aug. 6, 2020

(86) PCT No.: PCT/JP2020/030107
§ 371 (c)(1),
(2) Date: Jan. 28, 2022

(87) PCT Pub. No.: WO2021/029308
PCT Pub. Date: Feb. 18, 2021

(65) Prior Publication Data
US 2022/0287308 A1   Sep. 15, 2022

(30) Foreign Application Priority Data

Aug. 9, 2019 (JP) .................................. 2019-147693
Dec. 23, 2019 (JP) .................................. 2019-231507

(51) Int. Cl.
*A01N 43/90* (2006.01)
*A01P 7/04* (2006.01)
*C07D 498/14* (2006.01)

(52) U.S. Cl.
CPC ................ *A01N 43/90* (2013.01); *A01P 7/04* (2021.08); *C07D 498/14* (2013.01)

(58) Field of Classification Search
None
See application file for complete search history.

(56) References Cited

U.S. PATENT DOCUMENTS

| | | |
|---|---|---|
| 3,459,737 A | 8/1969 | Schmidt |
| 2017/0260199 A1* | 9/2017 | Hayashi ............... C07D 498/14 |

FOREIGN PATENT DOCUMENTS

| | | |
|---|---|---|
| JP | H0665206 A | 3/1994 |
| JP | 2007510707 A | 4/2007 |
| WO | 0125241 A2 | 4/2001 |
| WO | 2005044822 A1 | 5/2005 |
| WO | 2016027790 A1 | 2/2016 |

OTHER PUBLICATIONS

International Preliminary Report on Patentability, dated Feb. 8, 2022, for corresponding international application PCT/JP2020/030107 (1 page).
Notification Concerning Transmittal of International Preliminary Report on Patentability, mailed Feb. 17, 2022, for corresponding international application PCT/JP2020/030107 (1 page).
Notification of Transmittal of Translation of the International Preliminary Report on Patentability, mailed Feb. 17, 2022, for corresponding international application PCT/JP2020/030107 (1 page).
Written Opinion of the International Searching Authority, mailed Sep. 29, 2020, for corresponding international application PCT/JP2020/030107 (4 page).
International Search Report (ISR) mailed Sep. 29, 2020, issued for International application No. PCT/JP2020/030107. (2 pages).

* cited by examiner

*Primary Examiner* — Jeffrey S Lundgren
*Assistant Examiner* — Michael J Schmitt
(74) *Attorney, Agent, or Firm* — Law Office of Katsuhiro Arai

(57) ABSTRACT

A compound, or a salt thereof, is expressed by General Formula (1):

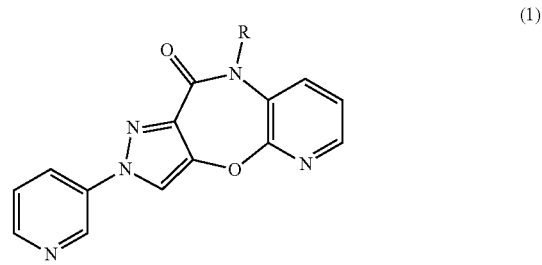

(1)

wherein R represents a $(C_1\text{-}C_6)$ alkoxy $(C_1\text{-}C_6)$ alkyl group, which is useful as an agricultural and horticultural insecticide with reduced harmful effects to animals including humans in production of agricultural, horticultural and other crops.

3 Claims, No Drawings

OXAZEPINONE DERIVATIVE, AGRICULTURAL/HORTICULTURAL INSECTICIDE CONTAINING THE SAME, AND METHOD FOR USING THE SAME

CROSS-REFERENCE TO RELATED APPLICATIONS

This application is the U.S. National Phase under 35 U.S.C. § 371 of International Application PCT/JP2020/030107, filed Aug. 6, 2020, which claims priority to Japanese Patent Application No. JP2019-147693, filed Aug. 9, 2019, and No. JP2019-231507, filed Dec. 23, 2019. The International Application was published under PCT Article 21(2) in a language other than English.

TECHNICAL FIELD

The present invention relates to an oxazepinone derivative, an agricultural/horticultural insecticide containing the derivative or salt thereof as its active ingredient, as well as a method for using the same.

BACKGROUND ART

Patent Literature 1 discloses that the oxazepinone derivative exhibits a high insecticidal activity against pest insects in agricultural/horticultural fields. However, this literature has no description about the specific structure of the compound proposed by the present invention, and also has no description about high safety for humans, etc., possessed by the compound of the present application.

CITATION LIST

Patent Literature

[Patent Literature 1] International Publication No. 2016/027790

SUMMARY OF INVENTION

Technical Problem

Pest insects, etc., are still causing serious damage to production of agricultural, horticultural and other crops, and due to the reasons such as emergence of pest insects that are resistant to existing chemicals, etc., there is a need to develop new agricultural/horticultural insecticides and miticides. In addition, due to the recent high interest in agricultural crop safety, there is a need to create agricultural/horticultural insecticides with reduced harmful effects to animals including humans.

Solution to Problem

Through repeated studies in earnest to develop a new agricultural/horticultural insecticide, the inventors of the present invention found that a compound or salt thereof expressed by General Formula (1) according to the present invention is an agricultural/horticultural insecticide having not only high effects of controlling pest insects in the agricultural/horticultural field but also high safety for humans, etc., and completed the present invention accordingly.

To be specific, the present invention relates to the following:

[1] A compound, or salt thereof, expressed by General Formula (1):

[chem 1]

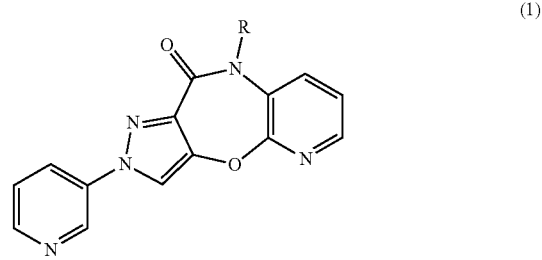

(1)

{in the formula, R represents a ($C_1$-$C_6$) alkoxy ($C_1$-$C_6$) alkyl group}.

[2] A compound, or salt thereof, according to [1] above, wherein R is a methoxymethyl group.

[3] An agricultural/horticultural insecticide characterized by containing, as an active ingredient, a compound or salt thereof according to [1] or [2] above.

[4] A method for use of agricultural/horticultural insecticide, characterized in that an agricultural/horticultural insecticide according to [3] above is applied to plants or soil by an effective amount.

[5] Use of a compound or salt thereof according to [1] or [2] above, as an agricultural/horticultural insecticide.

Advantageous Effects of Invention

The compound or salt thereof expressed by General Formula (1) as proposed by the present invention has excellent effects as an agricultural/horticultural insecticide. It is also effective on pest insects that live on dogs, cats, and other pets, or cows, sheep, and other livestock. Furthermore, the compound or salt thereof expressed by General Formula (1) according to the present invention has reduced harmful effects to animals including humans, and is thus very useful as a new agricultural/horticultural insecticide.

DESCRIPTION OF EMBODIMENTS

In the definition of General Formula (1) expressing the compound proposed by the invention of the present application, "($C_1$-$C_6$) alkyl group" represents, for example, a methyl group, ethyl group, normal propyl group, isopropyl group, normal butyl group, isobutyl group, secondary butyl group, tertiary butyl group, normal pentyl group, isopentyl group, tertiary pentyl group, neopentyl group, 2,3-dimethyl propyl group, 1-ethyl propyl group, 1-methyl butyl group, 2-methyl butyl group, normal hexyl group, isohexyl group, 2-hexyl group, 3-hexyl group, 2-methyl pentyl group, 3-methyl pentyl group, 1,1,2-trimethyl propyl group, 3,3-dimethyl butyl group, or other straight-chain or branched-chain alkyl group with a carbon atom number of 1 to 6.

"($C_1$-$C_6$) alkoxy group" represents, for example, a methoxy group, ethoxy group, normal propoxy group, isopropoxy group, normal butoxy group, secondary butoxy group, tertiary butoxy group, normal pentyloxy group, isopentyloxy group, tertiary pentyloxy group, neopentyloxy group, 2,3-dimethyl propyloxy group, 1-ethyl propyloxy group, 1-methyl butyloxy group, normal hexyloxy group, isohexyloxy group, 1,1,2-trimethyl propyloxy group, or other straight-chain or branched-chain alkoxy group with a carbon atom number of 1 to 6.

The expressions "($C_1$-$C_6$)," "($C_2$-$C_6$)," "($C_3$-$C_6$)," etc., each represent a range of carbon atom numbers for each of the various substitution groups. The aforementioned definition also applies to groups to which the aforementioned substitution groups are linked; for example, "($C_1$-$C_6$) alkoxy ($C_1$-$C_6$) alkyl group" indicates that a straight-chain or branched-chain alkoxy group with a carbon atom number of 1 to 6 is bonded to a straight-chain or branched-chain alkyl group with a carbon atom number of 1 to 6.

The salt of the compound expressed by General Formula (1) according to the present invention may be, for example, hydrochloride salt, sulfate salt, nitrate salt, phosphate salt or other salt of inorganic acid, acetate salt, fumarate salt, maleate salt, oxalate salt, methane sulfonate salt, benzene sulfonate salt, paratoluene sulfonate salt or other salt of organic acid, or salt made with a sodium ion, potassium ion, calcium ion, trimethyl ammonium, or other inorganic or organic base.

The compound or salt thereof expressed by General Formula (1) according to the present invention may have one or more asymmetric centers, or two or more types of optical isomers or diastereomers, in its structural formula, and the present invention covers individual optical isomers as well as all mixtures containing such optical isomers at any ratios. Also, the compound or salt thereof expressed by General Formula (1) according to the present invention may have two types of geometric isomers derived from carbon-carbon double bonds in its structural formula, and the present invention covers individual geometric isomers as well as all mixtures containing such geometric isomers at any ratios.

A preferable embodiment of the compound expressed by General Formula (1) according to the present invention is shown below.

Preferably R is a methoxymethyl group.

Various compounds according to the present invention can be manufactured using the manufacturing methods below, for example; however, the present invention is not limited to the following.

Manufacturing Method 1

[chem 2]

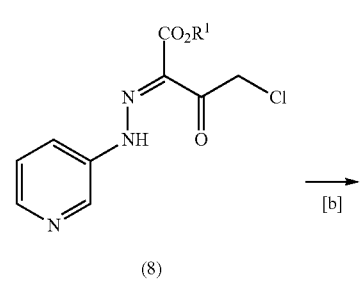

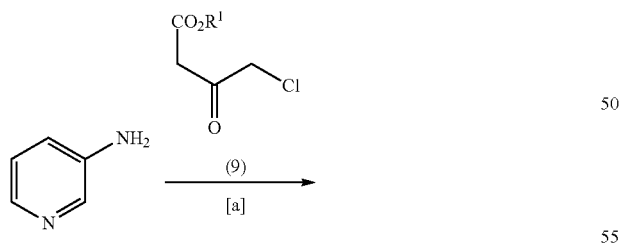

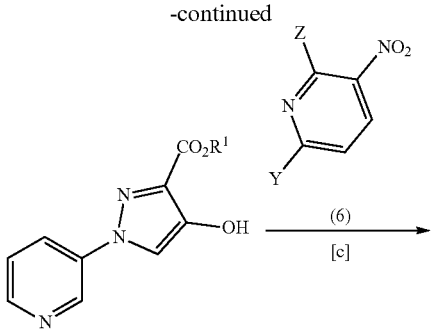

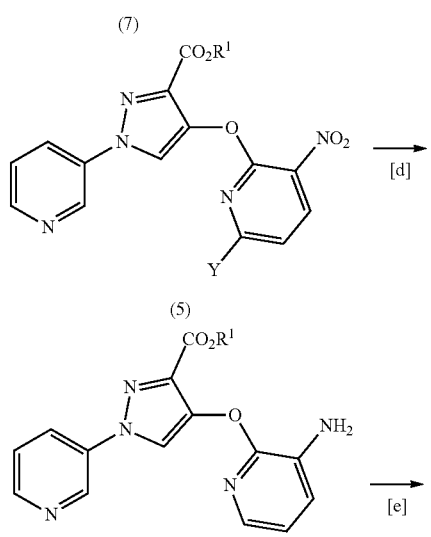

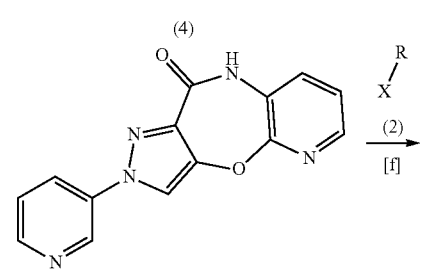

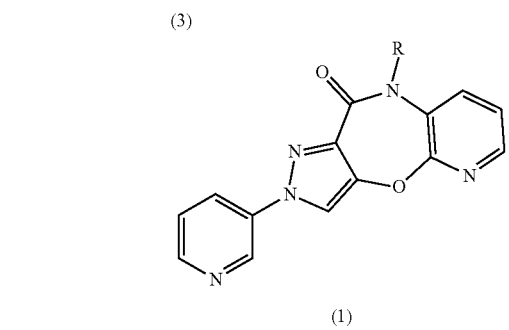

{in the formula, R is the same as mentioned above, $R^1$ represents a ($C_1$-$C_6$) alkyl group, X represents a halogen atom, a methanesulfonyloxy group, a paratoluenesulfonyloxy group, a trifluorosulfonyl group or other leaving group, Y represents a hydrogen atom or a halogen atom, and Z represents a halogen atom.}

The compound expressed by General Formula (1) according to the present invention can be manufactured from a 3-aminopyridine expressed by Formula (10) using Steps [a], [b], [c], [d], [e], and [f] below.

Step [a] A step of manufacturing a compound expressed by Formula (8) by subjecting the 3-aminopyridine expressed by Formula (10) to diazotization, and then causing the resultant to react with a 4-chloroaceto acetate expressed by Formula (9).

Step [b] A step of manufacturing a compound expressed by Formula (7) from the compound expressed by Formula (8) by a cyclization reaction.

Step [c] A step of manufacturing a compound expressed by Formula (5) by causing the compound expressed by Formula (7) to react with a 3-nitropyridine derivative expressed by Formula (6).

Step [d] A step of manufacturing a compound expressed by Formula (4) by reducing the nitro group of the compound expressed by Formula (5), and also by reducing "Y" in the formula when "Y" is a halogen atom.

Step [e] A step of manufacturing a compound expressed by Formula (3) from the compound expressed by Formula (4) by a cyclization reaction.

Step [f] A step of manufacturing the compound expressed by General Formula (1) according to the present invention by causing the compound expressed by Formula (3) to react with a compound expressed by Formula (2).

Manufacturing Method of Step [a]

The compound expressed by Formula (8) can be manufactured by causing the 3-aminopyridine expressed by Formula (10) to react with sodium nitrite in the presence of 6N hydrochloric acid for diazotization, and then by causing the resultant to react with the 4-chloroaceto acetate expressed by Formula (9) in the presence of a base and an inert solvent.

The base that can be used in this reaction may be, for example, lithium hydroxide, sodium hydroxide, potassium hydroxide, calcium hydroxide, or other hydroxide; lithium carbonate, lithium hydrogen carbonate, sodium carbonate, sodium hydrogen carbonate, potassium carbonate, potassium hydrogen carbonate, calcium carbonate, magnesium carbonate, cesium carbonate, or other carbonate; lithium acetate, sodium acetate, potassium acetate, or other acetate, etc., which is normally used by an amount in a range of 1.0 to 10 molar times relative to 1 mol of the 3-aminopyridine expressed by Formula (10).

The inert solvent that can be used in this reaction may be any solvent so long as it does not significantly inhibit the progression of this reaction, such as pentane, hexane, cyclohexane, or other chain or cyclic saturated hydrocarbon; benzene, toluene, xylene, or other aromatic hydrocarbon; diethyl ether, tetrahydrofuran (THF), dioxane, or other chain or cyclic ether; methylene chloride, chloroform, carbon tetrachloride, or other halogenated hydrocarbon; chlorobenzene, dichlorobenzene, or other halogenated aromatic hydrocarbon; acetonitrile or other nitrile; ethyl acetate or other ester; N,N-dimethyl formamide, N,N-dimethyl acetamide, dimethyl sulfoxide, 1,3-dimethyl-2-imidazolidinone or other polar solvent; methanol, ethanol, propanol, butanol, 2-propanol or other alcohol; water, etc., where any of these inert solvents may be used alone or two or more of them may be mixed together. This inert solvent may be normally used by any amount selected as deemed appropriate in a range of 0.1 to 100 L relative to 1 mol of the 3-aminopyridine expressed by Formula (10).

Since this reaction is an equimolar reaction, each compound only needs to be used by an equimolar amount; however, either compound may be used by an excessive amount. The reaction temperature of this reaction needs to be normally selected as anywhere between about 0° C. and the boiling point of the solvent used, and the reaction time, which varies depending on the reaction scale, the reaction temperature, etc., and which is not constant, may be normally selected as deemed appropriate in a range of several minutes to 48 hours. Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method of Step [b]

The compound expressed by Formula (7) can be manufactured from the compound expressed by Formula (8) by a cyclization reaction in the presence of a base and an inert solvent.

The base that can be used in this reaction may be, lithium diisopropylamide, lithium hexamethyldisilazane, sodium hexamethyldisilazane, or other organometallic compounds; sodium tertiary butoxide, potassium tertiary butoxide, or other alkoxide; sodium hydride, potassium hydride, or other metal hydride; lithium carbonate, lithium hydrogen carbonate, sodium carbonate, sodium hydrogen carbonate, potassium carbonate, potassium hydrogen carbonate, calcium carbonate, magnesium carbonate, cesium carbonate, or other carbonate; lithium acetate, sodium acetate, potassium acetate, or other acetate, etc. The base is normally used by an amount in a range of 1.0 to 10 molar times relative to 1 mol of the compound expressed by Formula (8).

The inert solvent that can be used in this reaction may be any solvent so long as it does not significantly inhibit the progression of this reaction, such as pentane, hexane, cyclohexane, or other chain or cyclic saturated hydrocarbon; benzene, toluene, xylene, or other aromatic hydrocarbon; diethyl ether, tetrahydrofuran (THF), dioxane, or other chain or cyclic ether, acetonitrile or other nitrile; ethyl acetate or other ester; N,N-dimethyl formamide, N,N-dimethyl acetamide, dimethyl sulfoxide, 1,3-dimethyl-2-imidazolidinone or other polar solvent; methanol, ethanol, propanol, butanol, 2-propanol or other alcohol, etc., where any of these inert solvents may be used alone or two or more of them may be mixed together. This inert solvent may be normally used by any amount selected as deemed appropriate in a range of 0.1 to 100 L relative to 1 mol of the compound expressed by Formula (8).

The reaction temperature of this reaction needs to be normally selected as anywhere between about 0° C. and the boiling point of the solvent used, and the reaction time, which varies depending on the reaction scale, the reaction temperature, etc., and which is not constant, may be selected as deemed appropriate in a range of several minutes to 48 hours. Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method of Step [c]

The compound expressed by Formula (5) can be manufactured by causing the compound expressed by Formula (7) to react with the compound expressed by Formula (6) in the presence of a base and an inert solvent.

The base that can be used in this reaction may be, for example, lithium diisopropylamide, lithium hexamethyldisilazane, sodium hexamethyldisilazane, or other organometallic compound; sodium tertiary butoxide, potassium tertiary butoxide, or other alkoxide; sodium hydride, potassium hydride, or other metal hydride; lithium hydroxide, sodium hydroxide, potassium hydroxide, calcium hydroxide, or other hydroxide; lithium carbonate, lithium hydrogen carbonate, sodium carbonate, sodium hydrogen carbonate, potassium carbonate, potassium hydrogen carbonate, calcium carbonate, magnesium carbonate, cesium carbonate, or other carbonate; lithium acetate, sodium acetate, potassium acetate, or other acetate, etc. The base is normally used by an amount in a range of 1.0 to 10 molar times relative to 1 mol of the compound expressed by Formula (7).

The inert solvent that can be used in this reaction may be any solvent so long as it does not significantly inhibit the progression of this reaction, such as pentane, hexane, cyclohexane, or other chain or cyclic saturated hydrocarbon; benzene, toluene, xylene, or other aromatic hydrocarbon; diethyl ether, tetrahydrofuran (THF), dioxane, or other chain or cyclic ether, acetonitrile or other nitrile; ethyl acetate or other ester; N,N-dimethyl formamide, N,N-dimethyl acetamide, dimethyl sulfoxide, 1,3-dimethyl-2-imidazolidinone or other polar solvent; etc., where any of these inert solvents may be used alone or two or more of them may be mixed together. This inert solvent may be normally used by any amount selected as deemed appropriate in a range of 0.1 to 100 L relative to 1 mol of the compound expressed by Formula (7).

Since this reaction is an equimolar reaction, each compound only needs to be used by an equimolar amount; however, either compound may be used by an excessive amount. The reaction temperature of this reaction needs to be normally selected as anywhere between about 0° C. and the boiling point of the solvent used, and the reaction time, which varies depending on the reaction scale, the reaction temperature, etc., and which is not constant, may be normally selected as deemed appropriate in a range of several minutes to 48 hours. Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method of Step [d]

The compound expressed by Formula (4) can be manufactured by reducing the nitro group of the compound expressed by Formula (5) by iron powder reduction reaction or hydrogenation reaction that is used as a normal method in synthetic organic chemistry.

Manufacturing Method of Step [e]

The compound expressed by Formula (3) can be manufactured from the compound expressed by Formula (4) by a cyclization reaction in the presence of a base and an inert solvent.

The base that can be used in this reaction may be lithium diisopropylamide, lithium hexamethyldisilazane, sodium hexamethyldisilazane, or other organometallic compound; sodium tertiary butoxide, potassium tertiary butoxide, or other alkoxide; sodium hydride, potassium hydride, or other metal hydride; etc. The base is normally used by an amount in a range of 1.0 to 10 molar times relative to 1 mol of the compound expressed by Formula (4).

The inert solvent that can be used in this reaction may be any solvent so long as it does not significantly inhibit the progression of this reaction, such as pentane, hexane, cyclohexane, or other chain or cyclic saturated hydrocarbon; benzene, toluene, xylene, or other aromatic hydrocarbon; diethyl ether, tetrahydrofuran (THF), dioxane, or other chain or cyclic ether, acetonitrile or other nitrile; ethyl acetate or other ester; N,N-dimethyl formamide, N,N-dimethyl acetamide, dimethyl sulfoxide, 1,3-dimethyl-2-imidazolidinone or other polar solvent; etc., where any of these inert solvents may be used alone or two or more of them may be mixed together. This inert solvent may be normally used by any amount selected as deemed appropriate in a range of 0.1 to 100 L relative to 1 mol of the compound expressed by Formula (4).

The reaction temperature of this reaction needs to be normally selected as anywhere between about 0° C. and the boiling point of the solvent used, and the reaction time, which varies depending on the reaction scale, the reaction temperature, etc., and which is not constant, may be selected as deemed appropriate in a range of several minutes to 48 hours. Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method of Step [f]

The compound expressed by General Formula (1) according to the present invention can be manufactured by causing the compound expressed by Formula (3) to react with the compound expressed by Formula (2) in the presence of a base and an inert solvent.

The base that can be used in this reaction may be lithium diisopropylamide, lithium hexamethyldisilazane, sodium hexamethyldisilazane, or other organometallic compound; sodium tertiary butoxide, potassium tertiary butoxide, or other alkoxide; sodium hydride, potassium hydride, or other metal hydride; etc. The base is normally used by an amount in a range of 1.0 to 10 molar times relative to 1 mol of the compound expressed by Formula (3).

The inert solvent that can be used in this reaction may be any solvent so long as it does not significantly inhibit the progression of this reaction, such as pentane, hexane, cyclohexane, or other chain or cyclic saturated hydrocarbon; benzene, toluene, xylene, or other aromatic hydrocarbon; diethyl ether, tetrahydrofuran (THF), dioxane, or other chain or cyclic ether, acetonitrile or other nitrile; ethyl acetate or other ester; N,N-dimethyl formamide, N,N-dimethyl acetamide, dimethyl sulfoxide, 1,3-dimethyl-2-imidazolidinone or other polar solvent; etc., where any of these inert solvents may be used alone or two or more of them may be mixed together. This inert solvent may be normally used by any amount selected as deemed appropriate in a range of 0.1 to 100 L relative to 1 mol of the compound expressed by Formula (3).

Since this reaction is an equimolar reaction, each compound only needs to be used by an equimolar amount; however, either compound may be used by an excessive amount. The reaction temperature of this reaction needs to be normally selected as anywhere between about 0° C. and the boiling point of the solvent used, and the reaction time, which varies depending on the reaction scale, the reaction temperature, etc., and which is not constant, may be normally selected as deemed appropriate in a range of several minutes to 48 hours. Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method 2

[chem 3]

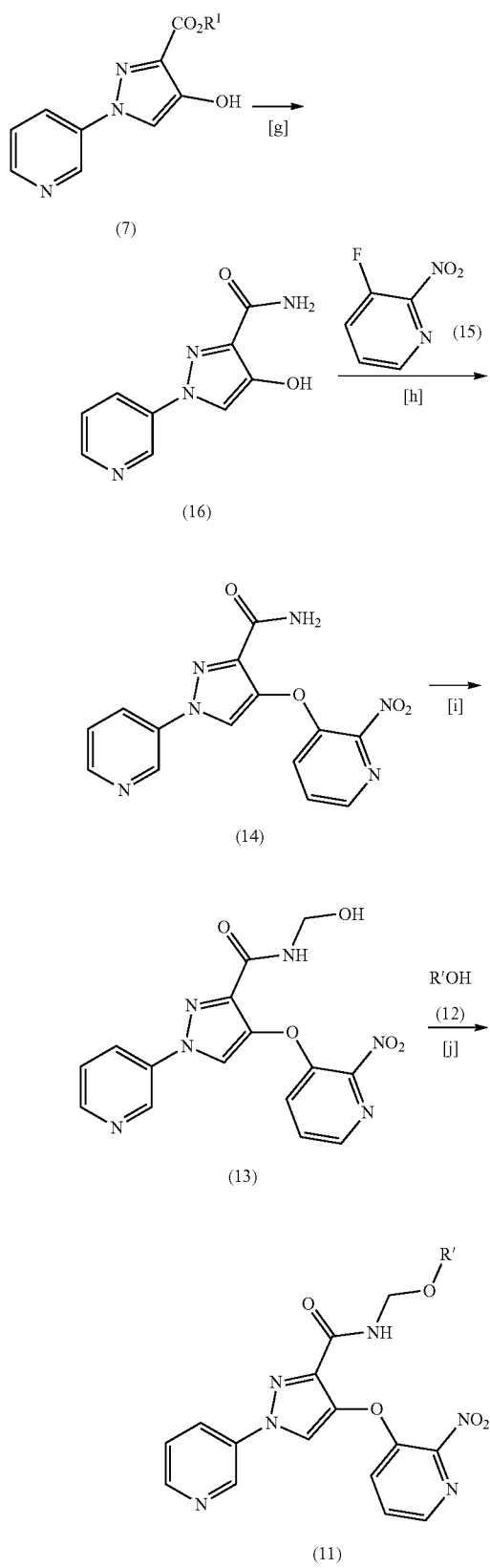

(7), (16), (14), (13), (11)

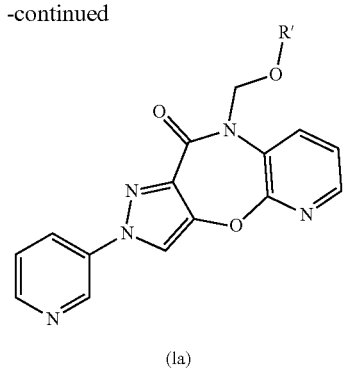

(1a)

{in the formula, $R^1$ is the same as mentioned above, and R' represents a ($C_1$-$C_6$) alkyl group.}

The compound expressed by General Formula (1a) included in General Formula (1) according to the present invention can be manufactured from the compound expressed by Formula (7) using Steps [g], [h], [i], [j], and [k] below.

Step [g] A step of manufacturing a compound expressed by Formula (16) by converting the ester group of the compound expressed by Formula (7) into an amide group.

Step [h] A step of manufacturing a compound expressed by Formula (14) by causing the compound expressed by Formula (16) to react with a compound expressed by Formula (15).

Step [i] A step of manufacturing a compound expressed by Formula (13) by treating the compound expressed by Formula (14) with formalin.

Step [j] A step of manufacturing a compound expressed by Formula (11) by causing the compound expressed by Formula (13) to react with a compound expressed by Formula (12).

Step [k] A step of manufacturing the compound expressed by General Formula (1a) included in General Formula (1) according to the present invention, from the compound expressed by Formula (11) by a cyclization reaction.

Manufacturing Method of Step [g]

The compound expressed by Formula (16) can be manufactured by treating the compound expressed by Formula (7) with aqueous ammonia in the presence of an inert solvent.

The inert solvent that can be used in this reaction may be any solvent so long as it does not significantly inhibit the progression of this reaction, such as N,N-dimethyl formamide, N,N-dimethyl acetamide, dimethyl sulfoxide, 1,3-dimethyl-2-imidazolidinone or other polar solvent; methanol, ethanol, propanol, butanol, 2-propanol or other alcohol; water, etc., where any of these inert solvents may be used alone or two or more of them may be mixed together.

The reaction temperature of this reaction needs to be normally selected as anywhere between about 0° C. and the boiling point of the solvent used, and the reaction time, which varies depending on the reaction scale, the reaction temperature, etc., and which is not constant, may be selected as deemed appropriate in a range of several minutes to 48 hours. Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method of Step [h]

The compound expressed by Formula (14) can be manufactured by causing the compound expressed by Formula (16) to react with the compound expressed by Formula (15) in the presence of a base and an inert solvent.

The base that can be used in this reaction may be, for example, lithium diisopropylamide, lithium hexamethyldisilazane, sodium hexamethyldisilazane, or other organometallic compound; sodium tertiary butoxide, potassium tertiary butoxide, or other alkoxide; sodium hydride, potassium hydride, or other metal hydride; lithium hydroxide, sodium hydroxide, potassium hydroxide, calcium hydroxide, or other hydroxide; lithium carbonate, lithium hydrogen carbonate, sodium carbonate, sodium hydrogen carbonate, potassium carbonate, potassium hydrogen carbonate, calcium carbonate, magnesium carbonate, cesium carbonate, or other carbonate; lithium acetate, sodium acetate, potassium acetate, or other acetate, etc. The base is normally used by an amount in a range of 1.0 to 10 molar times relative to 1 mol of the compound expressed by Formula (16).

The inert solvent that can be used in this reaction may be any solvent so long as it does not significantly inhibit the progression of this reaction, such as pentane, hexane, cyclohexane, or other chain or cyclic saturated hydrocarbon; benzene, toluene, xylene, or other aromatic hydrocarbon; diethyl ether, tetrahydrofuran (THF), dioxane, or other chain or cyclic ether, acetonitrile or other nitrile; ethyl acetate or other ester; N,N-dimethyl formamide, N,N-dimethyl acetamide, dimethyl sulfoxide, 1,3-dimethyl-2-imidazolidinone or other polar solvent; etc., where any of these inert solvents may be used alone or two or more of them may be mixed together. This inert solvent may be normally used by any amount selected as deemed appropriate in a range of 0.1 to 100 L relative to 1 mol of the compound expressed by Formula (16).

Since this reaction is an equimolar reaction, each compound only needs to be used by an equimolar amount; however, either compound may be used by an excessive amount. The reaction temperature of this reaction needs to be normally selected as anywhere between about 0° C. and the boiling point of the solvent used, and the reaction time, which varies depending on the reaction scale, the reaction temperature, etc., and which is not constant, may be normally selected as deemed appropriate in a range of several minutes to 48 hours. Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method of Step [i]

The compound expressed by Formula (13) can be manufactured by treating the compound expressed by Formula (14) with 37% formalin in the presence of a base and an inert solvent.

The base that can be used in this reaction may be, for example, lithium carbonate, lithium hydrogen carbonate, sodium carbonate, sodium hydrogen carbonate, potassium carbonate, potassium hydrogen carbonate, calcium carbonate, magnesium carbonate, cesium carbonate, or other carbonate; lithium acetate, sodium acetate, potassium acetate, or other acetate, etc. The base is normally used by an amount in a range of 1.0 to 10 molar times relative to 1 mol of the compound expressed by Formula (14).

The inert solvent that can be used in this reaction may be any solvent so long as it does not significantly inhibit the progression of this reaction, such as pentane, hexane, cyclohexane, or other chain or cyclic saturated hydrocarbon; benzene, toluene, xylene, or other aromatic hydrocarbon; diethyl ether, tetrahydrofuran (THF), dioxane, or other chain or cyclic ether, acetonitrile or other nitrile; ethyl acetate or other ester; N,N-dimethyl formamide, N,N-dimethyl acetamide, dimethyl sulfoxide, 1,3-dimethyl-2-imidazolidinone or other polar solvent; etc., where any of these inert solvents may be used alone or two or more of them may be mixed together. This inert solvent may be normally used by any amount selected as deemed appropriate in a range of 10 to 100 L relative to 1 mol of the compound expressed by Formula (14).

The reaction temperature of this reaction needs to be normally selected as anywhere between about 0° C. and the boiling point of the solvent used, and the reaction time, which varies depending on the reaction scale, the reaction temperature, etc., and which is not constant, may be selected as deemed appropriate in a range of several minutes to 48 hours. Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method of Step [j]

The compound expressed by Formula (11) can be manufactured by causing the compound expressed by Formula (13) to react with an alcohol expressed by Formula (12) as a solvent in the presence of oxalic acid.

The oxalic acid used in this reaction may be used by any amount selected as deemed appropriate in a range of 0.1 to 10 molar times relative to 1 mol of the compound expressed by Formula (13) such that the pH of the reaction solution reaches around 3.

The alcohol expressed by Formula (12) in this reaction may be normally used by any amount selected as deemed appropriate in a range of 10 to 100 L relative to 1 mol of the compound expressed by Formula (13).

The reaction temperature of this reaction needs to be normally selected as anywhere between about 0° C. and the boiling point of the solvent used, and the reaction time, which varies depending on the reaction scale, the reaction temperature, etc., and which is not constant, may be selected as deemed appropriate in a range of several minutes to 48 hours. Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method of Step [k]

The compound expressed by General Formula (1a) included in General Formula (1) according to the present invention can be manufactured from the compound expressed by Formula (11) by a cyclization reaction involving Smiles re-arrangement in the presence of a base and an inert solvent.

The base that can be used in this reaction may be, for example, sodium tertiary butoxide, potassium tertiary butoxide, or other alkoxide; etc., sodium hydride, potassium hydride, or other metal hydride; lithium hydroxide, sodium hydroxide, potassium hydroxide, calcium hydroxide, or other hydroxide; lithium carbonate, lithium hydrogen carbonate, sodium carbonate, sodium hydrogen carbonate, potassium carbonate, potassium hydrogen carbonate, calcium carbonate, magnesium carbonate, cesium carbonate, or other carbonate; lithium acetate, sodium acetate, potassium acetate, or other acetate, etc. The base is normally used by an amount in a range of 1.0 to 10 molar times relative to 1 mol of the compound expressed by Formula (11).

The inert solvent that can be used in this reaction may be any solvent so long as it does not significantly inhibit the progression of this reaction, such as pentane, hexane, cyclohexane, or other chain or cyclic saturated hydrocarbon; benzene, toluene, xylene, or other aromatic hydrocarbon; diethyl ether, tetrahydrofuran (THF), dioxane, or other chain or cyclic ether, acetonitrile or other nitrile; ethyl acetate or other ester; N,N-dimethyl formamide, N,N-dimethyl acetamide, dimethyl sulfoxide, 1,3-dimethyl-2-imidazolidinone or other polar solvent; etc., where any of these inert solvents may be used alone or two or more of them may be mixed together. This inert solvent may be normally used by any amount selected as deemed appropriate in a range of 0.1 to 100 L relative to 1 mol of the compound expressed by Formula (11).

The reaction temperature of this reaction needs to be normally selected as anywhere between about 0° C. and the boiling point of the solvent used, and the reaction time, which varies depending on the reaction scale, the reaction temperature, etc., and which is not constant, may be selected as deemed appropriate in a range of several minutes to 48 hours. Once the reaction is complete, the target substance may be isolated using any normal method from the reaction system that contains the target substance, and, if necessary, the isolated substance may be refined by means of recrystallization, column chromatography, etc., to manufacture the target substance.

The following illustrates representative examples of the compound expressed by General Formula (1) according to the present invention, in Table 1 below; it should be noted, however, that the present invention is not limited to these examples.

In the table, the physical property indicates the melting point (° C.), and the black circle in "R" means a binding site to a nitrogen atom in General Formula (1).

[chem 4]

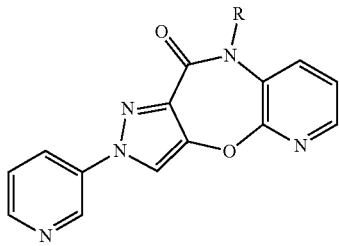

(1)

TABLE 1

| Compound No. | R | Physical property |
|---|---|---|
| 1-1 | ⌒O⌒ | 209-210 |
| 1-2 | ⌒O⌒ | 182-183 |
| 1-3 | ⌒O⌒ | — |
| 1-4 | ⌒O⋎ | — |

TABLE 1-continued

| Compound No. | R | Physical property |
|---|---|---|
| 1-5 | ⌒O⌒ | — |

An agricultural/horticultural insecticide containing, as its active ingredient, a compound or salt thereof expressed by General Formula (1) according to the present invention is suitable for controlling various pest insects, such as agricultural pest insects, forest pest insects, stored-grain pest insects, hygiene pest insects, nematodes, etc., that damage rice, fruit trees, vegetables, and other crops as well as flowers.

Examples of the aforementioned pest insects, nematodes, etc., include the following:

Lepidoptera pest insects include, for example, Aoiraga (*Parasa consocia*), Akakiriba (*Anomis mesogona*), Swallowtail (*Papilio xuthus*), Azukisayamushiga (*Matsumuraeses azukivora*), Azukinomeiga (*Ostrinia scapulalis*), Africa Spodoptera (*Spodoptera exempta*), Fall webworm (*Hyphantria cunea*), European corn borer (*Ostrinia furnacalis*), Armyworm (*Pseudaletia separata*), Clothes moth (*Tinea translucens*), Igusashinmushiga (*Bactra furfurana*), Straight swift (*Parnara guttata*), Rice leaf roller (*Marasmia exigua*), Inetsutomushi (*Parnara guttata*), Pink borer (*Sesamia inferens*), Imokibaga (*Brachmia triannulella*), Slug moth (*Monema flavescens*), Irakusaginuwaba (*Trichoplusia ni*), Ukonnomeiga (*Pleuroptya ruralis*), Umeedashaku (*Cystidia couaggaria*), Uranamishijimi (*Lampides boeticus*), Pellucid hawk moth (*Cephonodes hylas*), Tobacco budworm (*Helicoverpa armigera*), Ootobimonshachihoko (*Phalerodonta manleyi*), Oominoga (*Eumeta japonica*), Large white (*Pieris brassicae*), Lackey moth (*Malacosoma neustria testacea*), Kakinohetamushiga (*Stathmopoda masinissa*), Kakihosoga (*Cuphodes diospyrosella*), Apple leafroller (*Archips xylosteanus*), Turnip moth (*Agrotis segetum*), Kanshoshinkuihamaki (*Tetramoera schistaceana*), Swallowtail butterfly (*Papilio machaon hippocrates*), Macular bat (*Endoclyta sinensis*), Ginmonhamoguriga (*Lyonetia prunifoliella*), Kinmonhosoga (*Phyllonorycter ringoneella*), Kurimiga (*Cydia kurokoi*), Kurimidorishinkuiga (*Eucoenogenes aestuosa*), Grape berry moth (*Lobesia botrana*), Kuroshitaaoiraga (*Latoia sinica*), Kurofutamonmadarameiga (*Euzophera batangensis*), Kuwaihosohamaki (*Phalonidia mesotypa*), Mulberry tiger moth (*Spilosoma imparilis*), Kuwanomeiga (*Glyphodes pyloalis*), Kuwahimehamaki (*Olethreutes mori*), Common clothes moth (*Tineola bisselliella*), Swift moth (*Endoclyta excrescens*), European grain moth (*Nemapogon granellus*), Kosukashiba (*Synanthedon hector*), Codling moth (*Cydia pomonella*), Diamondback moth (*Plutella xylostella*), Rice leafroller (*Cnaphalocrocis medinalis*), Southern pink borer (*Sesamia calamistis*), Yellow stem borer (*Scirpophaga incertulas*), Shibatsutoga (*Pediasia teterrellus*), Potato moth (*Phthorimaea operculella*), Lobster moth (*Stauropus fagi persimilis*), Shiroichimonjimadarameiga (*Etiella zinckenella*), Beet armyworm (*Spodoptera exigua*), White ten bat (*Palpifer sexnotata*), Shironayotou (*Spodoptera mauritia*), Rice white giant pyralidae (*Scirpophaga innotata*), Shiromonyaga (*Xestia c-nigrum*), Sujikiriyotou (*Spodoptera depravata*), Mediterranean flour moth (*Ephestia kuehniella*), Orange moth (*Angerona prunaria*), Seguroshachihoko (*Clostera anastomosis*), Soybean looper (*Pseudoplusia includens*), Daizusayamushiga (*Matsumuraeses falcana*), Tobacco budworm (*Helicoverpa assulta*), Tamanaginuwaba (*Autographa nigrisigna*), Black cutworm (*Agrotis ipsilon*), Arm. Pseudoconspersa (*Euproctis pseudoconspersa*), Smaller tea tortix (*Adoxophyes orana*), Tea leafroller (*Caloptilia theivora*), Tea tortrix (*Homona magnanima*), Tobacco moth (*Ephestia elutella*), Chaminoga (*Eumeta minuscula*), Tsumaakashachihoko (*Clostera anachoreta*), Heliothis maritima (*Heliothis maritima*), Tenguhamaki (*Sparganothis pilleriana*), Toumorokoshimeiga (*Busseola fusca*), Tussock (*Euproctis subflava*), Tobimonooedashaku (*Biston robustum*), Tomato fruit worm (*Heliothis zea*), Nakajiroshitaba (*Aedia leucomelas*), Nashiiraga (*Narosoideus flavidorsalis*), Nashikenmon (*Viminia rumicis*), Nashichibiga (*Bucculatrix pyrivorella*), Oriental fruit moth (*Grapholita molesta*), Nashihosoga (*Spulerina astaurota*), Nashimadarameiga (*Ectomyelois pyrivorella*), Rice stem borer (*Chilo suppressalis*), Negikoga (*Acrolepiopsis sapporensis*), Indian meal moth (*Plodia interpunctella*), Haimadaranomeiga (*Hellula undalis*), Angoumois grain moth (*Sitotroga cerealella*), Common cutworm (*Spodoptera litura*), a kind of Tortricid (*Eucosma aporema*), Barahamaki (*Acleris comariana*), Himekuroiraga (*Scopelodes contractus*), Himeshiromondokuga (*Orgyia thyellina*), Fall armyworm (*Spodoptera frugiperda*), Fukinomeiga (*Ostrinia zaguliaevi*), Futaobikoyaga (*Naranga aenescens*), Futatenkagibamodoki (*Andraca bipunctata*), Grape clearwing moth (*Paranthrene regalis*), Grape sparrow (*Acosmeryx castanea*), Grape leafminer (*Phyllocnistis toparcha*), Grape hime moth (*Endopiza viteana*), Grape bombardier moth (*Eupoecillia ambiguella*), Velvet bean caterpillar (*Anticarsia gemmatalis*), Hosobahaiirohamaki (*Cnephasia cinereipalpana*), Gypsy moth (*Lymantria dispar*), Pine moth (*Dendrolimus spectabilis*), Soybean pod borer (*Leguminivora glycinivorella*), Legume pod borer (*Maruca testulalis*), Mamehimesayamushiga (*Matsumuraeses phaseoli*), Mamehosoga (*Caloptilia soyella*), Citrus leafminer (*Phyllocnistis citrella*), Maeusukinomeiga (*Omiodes indicata*), Midarekakumonhamaki (*Archips fuscocupreanus*), Mitsumonkinuwaba (*Acanthoplusia agnata*), Minoga (*Bambalina* sp.), Peach fruit moth (*Carposina niponensis*), Momonogomadaranomeiga (*Conogethes punctiferalis*), Momosukashiba (*Synanthedon* sp.), Momohamoguriga (*Lyonetia clerkella*), Monkiageha (*Papilio helenus*), Eastern pale clouded yellow (*Colias erate poliographus*), Monkuroshachihoko (*Phalera flavescens*), Cabbage butterfly (*Pieris rapae crucivora*), White butterfly such as cabbage butterfly (*Pieris rapae*), Gold-tail (*Euproctis similis*), Yamanoimokoga (*Acrolepiopsis suzukiella*), European corn borer (*Ostrinia nubilalis*), Cabbage armyworm (*Mamestra brassicae*), Yomogiedashaku (*Ascotis selenaria*), Yomogioohosohamaki (*Phtheochroides clandestina*), Ringooohamaki (*Hoshinoa adumbratana*), Ringokareha (*Odonestis pruni japonensis*), Ringokenmon (*Triaena intermedia*), Ringokokakumonhamaki (*Adoxophyes orana fasciata*), Ringokoshinkui (*Grapholita inopinata*), Ringoshirohimehamaki (*Spilonota ocellana*), Ringohaiirohamaki (*Spilonota lechriaspis*), Ringohamakikuroba (*Illiberis pruni*), Ringohimeshinkui (*Argyresthia conjugella*), Ringohosoga (*Caloptilia zachrysa*), Ringomonhamaki (*Archips breviplicanus*), Wataakakiriba (*Anomis flava*), Pink bollworm (*Pectinophora gossypiella*), Watanomeiga (*Notarcha derogata*), Wataherikuronomeiga (*Diaphania indica*), Tobacco budworm (*Heliothis virescens*), Wataringa (*Earias cupreoviridis*), and the like.

Hemiptera pest insects include, for example, Blue grasses stink bug (*Nezara antennata*), Sorghum plant bug (*Stenotus rubrovittatus*), Red streaks stink bug (*Graphosoma rubrolineatum*), Rice leaf bug (*Trigonotylus caelestialium*), etc., Akahimeherikamemushi (*Aeschynteles maculatus*), Akahoshikasumikame (*Creontiades pallidifer*), Red-spotted stink bug (*Dysdercus cingulatus*), Akahoshimarukaigaramushi (*Chrysomphalus ficus*), California red scale (*Aonidiella aurantii*), Large brown cicada (*Graptopsaltria nigrofuscata*), Chinch bug (*Blissusleucopterus*), Iseriya scale insects (*Icerya purchasi*), Unibanded stink bug (*Piezodorus hybneri*), Inekamemushi (*Lagynotomus elongatus*), Yellow rice leafhopper (*Thaia subrufa*), Black rice bug (*Scotinophara lurida*), Thorns aphid (*Sitobion ibarae*), Iwasaki stink bug (*Stariodes iwasakii*), Usuiromarukaigaramushi (*Aspidiotus destructor*), Usumonmidorikasumikame (*Taylorilygus pallidulus*), Umekobuaburamushi (*Myzusmumecola*), Plum white scale insects (*Pseudaulacaspis prunicola*), Pea aphid (*Acyrthosiphon pisum*), Okumoherikamemushi (*Anacanthocoris striicornis*), Okurotobikasumikame (*Ectometopterus micantulus*), Otogeshirahoshikamemushi (*Eysarcoris lewisi*), Oherikamemushi (*Molipteryx fuliginosa*), Ooyokobai (*Cicadella viridis*), Okabonoakaaburamushi (*Rhopalosophum rufiabdominalis*), Oribukatakaigaramushi (*Saissetia oleate*), Greenhouse whitefly (*Trialeurodes vaporariorum*), Kashihimeyokobai (*Aguriahana quercus*), Kasumi stink bugs (*Lygus* spp.), Kabawatafukimadaraaburamushi (*Euceraphis punctipennis*), Kankitsukaigaramushi (*Andaspis kashicola*), Kankitsukatakaigaramushi (*Coccus pseudomagnoliarum*), Oriental chinch bug (*Cavelerius saccharivorus*), Kikugunbai (*Galeatus spinifrons*), Kikuhimehigenagaaburamushi (*Macrosiphoniella sanborni*), Kimarukaigaramushi (*Aonidiella citrina*), Brown marmorated stink bug (*Halyomorpha mista*), Kusugunbai (*Stephanitis fasciicarina*), Kusutogarikijirami (*Trioza camphorae*), Rice bug (*Leptocorisa chinensis*), Kuritogarikijirami (*Trioza quercicola*), Kurumigunbai (*Uhlerites latius*), Grape leaf hopper (*Erythroneura comes*), Kuroashihosonagakamemushi (*Paromius exiguus*), Kurokatamarukaigaramushi (*Duplaspidiotus claviger*), Kurosujitsumaguroyokobai (*Nephotettix nigropictus*), Kurotobikasumikame (*Halticiellus insularis*), Sugarcane leafhopper (*Perkinsiella saccharicida*), Kuroringokijirami (*Psylla malivorella*), Mulberry psyllid (*Anomomeura mori*), Comstock mealybug (*Pseudococcus longispinis*), Mulberry white scale insects (*Pseudaulacaspis pentagona*), White peach scale insects (*Pulvinaria kuwacola*), Koaokasumikame (*Apolygus lucorum*), Kobanehyotannagakamemushi (*Togo hemipterus*), Komikanaburamushi (*Toxoptera aurantii*), Satokibikonakaigaramushi (*Saccharicoccus sacchari*), Satokibinewatamushi (*Geoica lucifuga*), Satonousuirounka (*Numata muiri*), Sanhozekaigaramushi (*Comstockaspis perniciosa*), Citrus snow scale (*Unaspis citri*), Potato aphid (*Aulacorthum solani*), Shirahoshi stink bug (*Eysarcoris ventralis*), Silverleaf whitefly (*Bemisia argentifolii*), Shirooyokobai (*Cicadella spectra*), Shiromarukaigaramushi (*Aspidiotus hederae*), Sukashihimeherikamemushi (*Liorhyssus hyalinus*), Segurohimekijirami (*Calophya nigridorsalis*), Sejirounka (*Sogatella furcifera*), Broad bean aphid (*Megoura crassicauda*), Radish aphid (*Brevicoryne brassicae*), Soybean aphid (*Aphis glycines*), Taiwankumoherikamemushi (*Leptocorisa oratorius*), Taiwantsumaguroyokobai (*Nephotettix virescens*), Taiwanhigenagaaburamushi (*Uroeucon formosanum*), Tabakokasumikame (*Cyrtopeltis tennuis*), Whitefly (*Bemisia tabaci*), Chanokatakaigaramushi (*Lecanium persicae*), Chanokurohoshikaigaramushi (*Parlatoria theae*), Chanomarukaigaramushi (*Pseudaonidia paeoniae*), Tea green leafhopper (*Empoasca onukii*), Brown winged green stink (*Plautia stali*), Churippuneaburamushi (*Dysaphis tulipae*), Tomato phid (*Macrosiphum euphorbiae*), Azalea lace bug (*Stephanitis pyrioides*), Indian wax scale (*Ceroplastes ceriferus*), Tsubakikurohoshikaigaramushi (*Parlatoria camelliae*), Tsumaguroaokasumikame (*Apolygus spinolai*), Green rice leafhopper (*Nephotettix cincticeps*), Tsuyaaokamemushi (*Glaucias subpunctatus*), Tensaikasumikame (*Orthotylus flavosparsus*), Corn aphid (*Rhopalosiphum maidis*), Corn planthopper (*Peregrinus maidis*), White-spotted spined bug (*Eysarcoris parvus*), bed bugs (*Cimex lectularius*), Todokijirami (*Psylla abieti*), Brown planthopper (*Nilaparvata lugens*), Toberakijirami (*Psylla tobirae*), Cabbage bug (*Eurydema rugosum*), Pear aphid (*Schizaphis piricola*), Nashikijirami (*Psylla pyricola*), Nashikurohoshikaigaramushi (*Parlatoreopsis pyri*), Nashigunbai (*Stephanitis nashi*), Nashikonakaigaramushi (*Dysmicoccus wistariae*), Nashishironagakaigaramushi (*Lepholeucaspis japonica*), Nashimaruaburamushi (*Sappaphis phi*), Turnip aphid (*Lipaphis erysimi*), Green onion aphid (*Neotoxoptera formosana*), Hasukubireaburamushi (*Rhopalosophum nymphaeae*), Rose leafhopper (*Edwardsianarosae*), Harannagakaigaramushi (*Pinnaspisaspidistrae*), Hannokijirami (*Psylla alni*), Hannonagayokobai (*Speusotettix subfusculus*), Hannohimeyokobai (*Alnetoidia alneti*), Panicum planthopper (*Sogatella panicicola*), Higenagakasumikame (*Adelphocoris lineolatus*), Himeakahoshikamemushi (*Dysdercus poecilus*), Himekurokaigaramushi (*Parlatoria ziziphi*), Himegunbai (*Uhlerites debile*), Small brown planthopper (*Laodelphax striatellus*), Himenagame (*Eurydema pulchrum*), Himeharikamemushi (*Cletus trigonus*), Himefutatennagaawafuki (*Clovia punctata*), Himeyokobai (*Empoasca* sp.), Hiratakatakaigaramushi (*Coccus hesperidum*), Hiratahyotannagakamemushi (*Pachybrachius luridus*), Japanese mealybug (*Planococcus kraunhiae*), Timothy plant bug (*Stenotus binotatus*), Futatenhimeyokobai (*Arboridia apicalis*), Futatenyokobai (*Macrosteles fascifrons*), Sloe bug (*Dolycoris baccarum*), Buchihigekurokasumikame (*Adelphocoris triannulatus*), Phylloxera (*Viteus vitifolii*), Ground cherry stink bug (*Acanthocoris sordidus*), Hosokumoherikamemushi (*Leptocorisa acuta*), Hosokobanenagakamemushi (*Macropes obnubilus*), Hosoharikamemushi (*Cletus punctiger*), Bean bug (*Riptortus clavatus*), Potetopishirido (*Paratrioza cockerelli*), Maekiawafuki (*Aphrophora costalis*), Japanese tarnished plant bug (*Lygus disponsi*), Madarakasumikame (*Lygus saundersi*), Matsukonakaigaramushi (*Crisicoccus pini*), Pine leafhopper (*Empoasca abietis*), Matsumotokonakaigaramushi (*Crisicoccus matsumotoi*), Bean aphid (*Aphis craccivora*), Plataspid bug (*Megacopta punctatissimum*), Marushirahoshikamemushi (*Eysarcoris guttiger*), Purple scale insects (*Lepidosaphes beckii*), Asian citrus psyllid (*Diaphorina citri*), Mikankuroaburamushi (*Toxoptera citricidus*), Mikankonakaigaramushi (*Planococcus citri*), Citrus whitefly (*Dialeurodes citri*), Orange spiny whitefly (*Aleurocanthus spiniferus*), Mikanhimekonakaigaramushi (*Pseudococcus citriculus*), Mikanhimeyokobai (*Zyginella citri*), Mikanhimewatakaigaramushi (*Pulvinaria citricola*), Mikanhiratakaigaramushi (*Coccus discrepans*), Mikanmarukaigaramushi (*Pseudaonidia duplex*), Mikanwatakaigaramushi (*Pulvinaria aurantii*), European fruit lecanium (*Lecanium corni*), Southern blue stink bug (*Nezara viridula*), Wheat leaf bug (*Stenodema calcaratum*), Oat bird-cherry aphid (*Rhopalosiphum padi*), Mugihigenagaaburamushi (*Sitobion akebiae*), Wheat green aphid (*Schizaphis graminum*), Mugiyokobai (*Sorhoanus tritici*), Peach leaf-curl aphid (*Brachycaudus helichrysi*), Purple stink bug (*Carpocoris purpureipennis*), Green peach aphid (*Myzus persicae*), Mealy plum aphid (*Hyalopterus pruni*), Yanagiaburamushi (*Aphis farinose yanagicola*), Yanagigunbai (*Metasalis populi*), Arrowhead scale (*Unaspis yanonensis*), Yamaasakijirami (*Mesohomotoma camphorae*), Yukiyanagiaburamushi (*Aphis spiraecola*), Apple aphid (*Aphis pomi*), Oystershell scale insects (*Lepidosaphes ulmi*), Ringokijirami (*Psylla mali*), Ringokurokasumikame (*Heterocordylus flavipes*), Ringokobuaburamushi (*Myzus malisuctus*), Ringoneaburamushi (*Aphidonuguis mali*), Apple leafhopper (*Orientus ishidai*), Apple green aphid (*Ovatus malicolens*), Woolly apple aphid (*Eriosoma lanigerum*), Red wax scale (*Ceroplastes rubens*), Cotton aphid (*Aphis gossypii*), and the like.

Coleoptera pest insects include, for example, Aosujikamikiri (*Xystrocera globosa*), Aobaarigatahanekakushi (*Paederus fuscipes*), Aohanamuguri (*Eucetonia roelofsi*), Adzuki bean weevil (*Callosobruchus chinensis*), Sweet potato weevil (*Cylas formicarius*), alfalfa weevil (*Hypera postica*), Rice plant weevil (*Echinocnemus squameus*), Inedorooimushi (*Oulema oryzae*), Inenekuihamushi (*Donacia provosti*), Rice water weevil (*Lissorhoptrus oryzophilus*), Sweet potato leaf beetle (*Colasposoma dauricum*), West Indian sweet potato weevil (*Euscepes postfasciatus*), Mexican bean beetle (*Epilachna varivestis*), Common beans weevil (*Acanthoscelides obtectus*), Western corn rootworm (*Diabrotica virgifera virgifera*), Umechokkirizoumushi (*Involvulus cupreus*), Cucurbit leaf beetle (*Aulacophora femoralis*), Pea weevil (*Bruchus pisorum*), Large twenty-eight-spotted ladybird (*Epilachna vigintioctomaculata*), Corn-sap beetle (*Carpophilus dimidiatus*), Tortoise beetle (*Cassida nebulosa*), Kiashinomihamushi (*Luperomorpha tunebrosa*), Striped flea beetle (*Phyllotreta striolata*), Yellow-spotted longicorn beetle (*Psacothea hilaris*), Kimadarakamikiri (*Aeolesthes chrysothrix*), Chestnut weevil (*Curculio sikkimensis*), Dried-fruit beetle (*Carpophilus hemipterus*), Citrus flower chafer (*Oxycetonia jucunda*), Corn rootworm (*Diabrotica* spp.), Gold beetles (*Mimela splendens*), Maize weevil (*Sitophilus zeamais*), Red flour beetle (*Tribolium castaneum*), Rice weevil (*Sitophilus oryzae*), Kohimekokunusutomodoki (*Palorus subdepressus*), Melolonthid (*Melolontha japonica*), Gomadarakamikiri (*Anoplophora malasiaca*), Mealworm (*Neatus picipes*), Colorado potato beetle (*Leptinotarsa decemlineata*), Southern corn rootworm (*Diabrotica undecimpunctata howardi*), Hunting billbug (*Sphenophorus venatus*), Jyushihoshikubinagahamushi (*Crioceris quatuordecimpunctata*), Plums weevil (*Conotrachelus nenuphar*), Daikonsaruzoumushi (*Ceuthorhynchidius albosuturalis*), Radish leaf beetle (*Phaedon brassicae*), Cigarette beetle (*Lasioderma serricorne*), Chibikofukizoumushi (*Sitona japonicus*), Chairokogane (*Adoretus tenuimaculatus*), Yellow mealworm (*Tenebrio molitor*), Chairosaruhamushi (*Basilepta balyi*), Clover leaf weevil (*Hypera nigrirostris*), Tensaitobihamushi (*Chaetocnema concinna*), Cupreous chafer (*Anomala cuprea*), Nagachakogane (*Heptophylla picea*), Nijuuyahoshi beetle (*Epilachna vigintioctopunctata*), Northern corn rootworm (*Diabrotica longicornis*), Flower beetle (*Eucetonia pilifera*), Wireworms (*Agriotes* spp.), Black carpet beetle (*Attagenus unicolor japonicus*), Bean leaf beetle (*Pagria signata*), Rufocuprea (*Anomala rufocuprea*), Himekokunusutomodoki (*Palorus ratzeburgii*), Black fungus beetle (*Alphitobius laevigatus*), Himemaru carpet beetle (*Anthrenus verbasci*), Hiratakikuimushi (*Lyctus brunneus*), Confused flour beetle (*Tribolium confusum*), Futasujihimehamushi (*Medythia nigrobilineata*), Budoutorakamikiri (*Xylotrechus pyrrhoderus*), Potato free Beetle (*Epitrix cucumeris*), Pine bark beetle (*Tomicus piniperda*), Japanese pine sawyer (*Monochamus alternatus*), Japanese beetle (*Popillia japonica*), Beans tiger beetle (*Epicauta gorhami*), Maize weevil (*Sitophilus zeamais*), Momochokkirizoumushi (*Rhynchites heros*), Vegetable weevil (*Listroderes costirostris*), Cowpea weevil (*Callosobruchus macu-

*latus*), Ringokofukizoumushi (*Phyllobius armatus*), Ringohanazoumushi (*Anthonomus pomorum*), Rurihamushi (*Linaeidea aenea*), Boll weevil (*Anthonomus grandis*), and the like.

Diptera pest insects include, for example, Common house mosquito (*Culex pipiens pallens*), Beetfly (*Pegomya hyoscyami*), South American leafminer (*Liriomyza huidobrensis*), Housefly (*Musca domestica*), Inekimoguribae (*Chlorops oryzae*), Inekukimigiwabae (*Hydrellia sasakii*), Rice leafminer (*Agromyza oryzae*), Inehime leafminer (*Hydrellia griseola*), Inehime leafminer (*Hydrellia griseola*), Ingenmoguribae (*Ophiomyia phaseoli*), Melon fly (*Dacus cucurbitae*), Spotted-wing drosophila (*Drosophila suzukii*), Japanese cherry fruit fly (*Rhacochlaena japonica*), False stable fly (*Muscina stabulans*), Nomibae such as Okimonnomibae (*Megaselia spiracularis*), Oochobae (*Clogmia albipunctata*), Kiriujigagambo (*Tipula aino*), Kurokinbae (*Phormia regina*), Kogataakaieka (*Culex tritaeniorhynchus*), Chinese *anopheles* (*Anopheles sinensis*), Daikonbae (*Hylemya brassicae*), Soybean pod gall midge (*Asphondylia* sp.), Seed-corn fly (*Delia platura*), Onion maggot (*Delia antiqua*), European cherry fruit fly (*Rhagoletis cerasi*), Autogenic house mosquito (*Culex pipiens molestus Forskal*), Mediterranean fruit fly (*Ceratitis capitata*), Chibikurobanekinokobae (*Bradysia agrestis*), Tensaimogurihanabae (*Pegomya cunicularia*), Tomato leafminer (*Liriomyza sativae*), Eggplant leafminer (*Liriomyza bryoniae*), Namoguribae (*Chromatomyia horticola*), Green onion leafminer (*Liriomyza chinensis*), Tropical house mosquitos (*Culex quinquefasciatus*), Yellow-fever mosquitos (*Aedes aegypti*), Tiger mosquito (*Aedes albopictus*), Beans leafminer (*Liriomyza trifolii*), Tomato leafminer (*Liriomyza sativae*), Oriental fruit fly (*Dacus dorsalis*), Japanese orange fly (*Dacus tsuneonis*), Wheat red gall midge (*Sitodiplosis mosellana*), Wheat stem maggot (*Meromuza nigriventris*), Mexican fruit fly (*Anastrepha ludens*), Apple maggot fly (*Rhagoletis pomonella*), and the like.

Hymenoptera pest insects include, for example, Amimeari (*Pristomyrmex pungens*), Bethylidae such as Little black ant (*Monomorium pharaohnis*), Oozuari (*Pheidole noda*), Turnip sawfly (*Athalia rosae*), Chestnut gall wasp (*Dryocosmus kuriphilus*), Negro ant (*Formica fusca japonica*), Vespids, Black-backed turnip sawfly (*Athalia infumata infumata*), Churenji sawfly (*Arge pagana*), Japanese neep sawfly (*Athalia japonica*), Leaf-cutting ant (*Acromyrmex* spp.), Fire ant (*Solenopsis* spp.), Ringohabachi (*Arge mali*), Ruriari (*Ochetellus glaber*), and the like.

Orthoptera pest insects include, for example, Ruspolia lineosa (*Homorocoryphus lineosus*), Mole cricket (*Gryllotalpa* sp.), Koinago (*Oxya hyla intricata*), Rice grasshopper (*Oxya yezoensis*), migratory locust (*Locusta migratoria*), Japanese grasshopper (*Oxya japonica*), Himekusakiri (*Homorocoryphus jezoensis*), Emma field cricket (*Teleogryllus emma*), and the like.

Thysanoptera pest insects include, for example, Akaobi thrips (*Selenothrips rubrocinctus*), Rice thrips (*Stenchaetothrips biformis*), Inekuda thrips (*Haplothrips aculeatus*), Kakikuda thrips (*Ponticulothrips diospyrosi*), Kiirohana thrips (*Thrips flavus*), Kusakiiro thrips (*Anaphothrips obscurus*), Kusukuda thrips (*Liothrips floridensis*), Gladiolus thrips (*Thrips simplex*), Kurogehana thrips (*Thrips nigropilosus*), Croton thrips (*Heliothrips haemorrhoidalis*), Mulberry thrips (*Pseudodendrothrips mori*), Cosmos thrips (*Microcephalothrips abdominalis*), Shiionagakuda thrips (*Leeuwenia pasanii*), Shiimarukuda thrips (*Litotetothrips pasaniae*), Citrus thrips (*Scirtothrips citri*), Sinakuda thrips (*Haplothrips chinensis*), Daizu thrips (*Mycterothrips glycines*), Daizuusuiro thrips (*Thrips setosus*), Chanokiiro thrips (*Scirtothrips dorsalis*), Chanokuro thrips (*Dendrothrips minowai*), Tsumekusakuda thrips (*Haplothrips niger*), Negi thrips (*Thrips tabaci*), Negikuro thrips (*Thrips alliorum*), Hana thrips (*Thrips hawaiiensis*), Hana Kuda thrips (*Haplothrips kurdjumovi*), Higebuto thrips (*Chirothrips manicatus*), Flower thrips (*Frankliniella intonsa*), Loquat Hana thrips (*Thrips coloratus*), Western flower thrips (*Franklinella occidentalis*), Minamikiiro thrips (*Thrips palmi*), Yurikiiro thrips (*Frankliniella lilivora*), Yurinokuda thrips (*Liothrips vaneeckei*), and the like.

Acari pest insects include, for example, Blue chiggers (*Leptotrombidium akamushi*), Ashinowahadani (*Tetranychus ludeni*), American dock tick (*Dermacentor variabilis*), Ishiinami spider mites (*Tetranychus truncatus*), House dust mite (*Ornithonyssus bacoti*), Demodex mite (*Demodex canis*), Cherry spider mites (*Tetranychus viennensis*), Kanzawa spider mite (*Tetranychus kanzawai*), ticks such as Brown dog tick (*Rhipicephalus sanguineus*), Stag tsumedani (*Cheyletus malaccensis*), Tyrophagus dimidiatus (*Tyrophagus putrescentiae*), American house dust mite (*Dermatophagoides farinae*), Redback spider (*Latrodectus hasseltii*), Taiwankaku ticks (*Dermacentor taiwanicus*), Chanonagasabi mite (*Acaphylla theavagrans*), Broad mite (*Polyphagotarsonemus latus*), Tomato russet mite (*Aculops lycopersici*), Northern fowl mite (*Ornithonyssus sylvairum*), Two-spotted spider mite (*Tetranychus urticae*), Nisenashisabi mite (*Eriophyes chibaensis*), Scabies mites (*Sarcoptes scabiei*), Futatogechimadani (*Haemaphysalis longicomis*), Black legged tick (*Ixodes scapularis*), Tyrophagus dimidiatus (*Tyrophagus similis*), Hosotsumedani (*Cheyletus eruditus*), Citrus red mite (*Panonychus citri*), Minami tsumedani (*Cheyletus moorei*), Minami hime spider mites (*Brevipalpus phoenicis*), Mimihizen mites (*Octodectes cynotis*), European house dust mite (*Dermatophagoides ptrenyssnus*), Yamatochimadani (*Haemaphysalis flava*), Ixodes ovatus (*Ixodes ovatus*), Ryukyu tangerine rust mite (*Phyllocoptruta citri*), Apple rust mite (*Aculus schlechtendali*), European red mite (*Panonychus ulmi*), Loan star tick (*Amblyomma americanum*), and Chicken mites (*Dermanyssus gallinae*), Robinnedani (*Rhyzoglyphus robini*), a kind of Nedanimodoki (*Sancassania* sp.), and the like.

Isoptera pest insects include, for example, Amami termite (*Reticulitermes miyatakei*), the United States drywood termites (*Incisitermes minor*), Formosan subterranean termite (*Coptotermes formosanus*), giant termite (*Hodotermopsis japonica*), Kanmon termite (*Reticulitermes* sp.), Kiashishiroari (*Reticulitermes flaviceps amamianus*), Kushimoto termite (*Glyptotermes kushimensis*), Koushu formosan subterranean termite (*Coptotermes guangzhoensis*), Koushun termite (*Neotermes koshunensis*), Kodama termite (*Glyptotermes kodamai*), Satsuma termite (*Glyptotermes satsumensis*), Daikoku termite (*Cryptotermes domesticus*), Taiwan termite (*Odontotermes formosanus*), Nakajima termite (*Glyptotermes nakajimai*), Nitobe termite (*Pericapritermes nitobei*), Yamato termite (*Reticulitermes speratus*), and the like.

Blattodea pest insects include, for example, Smokybrown cockroach (*Periplaneta fuliginosa*), German cockroach (*Blattella germanica*), Oriental cockroach (*Blatta orientalis*), Brown cockroach (*Periplaneta brunnea*), Hime German cockroach (*Blattella lituricollis*), Japanese cockroach (*Periplaneta japonica*), American cockroach (*Periplaneta americana*), and the like.

Siphonaptera include, for example, Human flea (*Pulex irritans*), Cat flea (*Ctenocephalides felis*), Chicken flea (*Ceratophyllus gallinae*), and the like.

Nematodes include, for example, Strawberry nematode (*Nothotylenchus acris*), Ineshingare nematode (*Aphelenchoides besseyi*), Northern meadow nematode (*Pratylenchus penetrans*), Northern root-knot nematode (*Meloidogyne hapla*), Sweet potato root-knot nematode (*Meloidogyne incognita*), Potato cyst nematode (*Globodera rostochiensis*), Java root-knot nematode (*Meloidogyne javanica*), Soybean cyst nematode (*Heterodera glycines*), Southern meadow nematode (*Pratylenchus coffeae*), Wheat meadow nematode (*Pratylenchus neglectus*), Mandarin orange root nematodes (*Tylenchus semipenetrans*), and the like.

Molluscs include, for example, Apple snail (*Pomacea canaliculata*), Giant African snail (*Achatina fulica*), Slugs (*Meghimatium bilineatum*), Chaco slug (*Lehmannina valentiana*), Kouranamekuji (*Limax flavus*), Siebold's globular snail (*Acusta despecta sieboldiana*), and the like.

In addition, the agricultural/horticultural insecticide proposed by the present invention has strong insecticidal effects on other pest insects such as tomato leaf miner (*Tuta absoluta*).

In addition, zoobiotic mites, which can also be controlled, include, for example, ticks such as *Rhipicephalus microplus* (*Boophilus microplus*), Brown dog tick (*Rhipicephalus sanguineus*), Futatogechimadani (*Haemaphysalis longicornis*), Kichimadani (*Haemaphysalis flava*), Adenophora chimadani (*Haemaphysalis campanulata*), Isukachimadani (*Haemaphysalis concinna*), Yamatochimadani (*Haemaphysalis japonica*), Higenagachimadani (*Haemaphysalis kitaokai*), lyasuchi tick (*Haemaphysalis ias*), Ixodes ovatus (*Ixodes ovatus*), Tanegata tick (*Ixodes nipponensis*), Schulze ticks (*Ixodes persulcatus*), Takasago Kirara ticks (*Amblyomma testudinarium*), Ootogechimadani (*Haemaphysalis megaspinosa*), Aminokaku ticks (*Dermacentor reticulatus*), and Taiwankaku ticks (*Dermacentor taiwanesis*), Torisashidani such as Chicken mites (*Dermanyssus gallinae*), Northern fowl mite (*Ornithonyssus sylviarum*), and Tropical fowl mite (*Ornithonyssus bursa*), chiggers such as Nanyo chiggers (*Eutrombicula wichmanni*), Scrub typhus mite (*Leptotrombidium akamushi*), Off thorns chiggers (*Leptotrombidium pallidum*), Fuji chiggers (*Leptotrombidium fuji*), Tosa chiggers (*Leptotrombidium tosa*), Europe Aki mite (*Neotrombicula autumnalis*), America chiggers (*Eutrombicula alfreddugesi*), and Miyagawa Tama chiggers (*Helenicula miyagawai*), Tsumedani such as Inutsumedani (*Cheyletiella yasguri*), Rabbit tsumedani (*Cheyletiella parasitivorax*), and Nekotsumedani (*Cheyletiella blakei*), Sarcoptes such as Rabbit mite (*Psoroptes cuniculi*), Ushishokuhidani (*Chorioptes bovis*), Dog ear mites (*Octodectes cynotis*), Scabies mites (*Sarcoptes scabiei*), and Cat foraminous mites (*Notoedres cati*), Demodex such as Demodex mite (*Demodex canis*) kind, and the like.

Fleas, which can also be controlled, include, for example, ectoparasitic apterous insects in the Siphonaptera order, or specifically, fleas belonging to the Pulicidae family and Ceratephyllus family, among others. Fleas belonging to the Pulicidae family include, for example, Dog flea (*Ctenocephalides canis*), Cat flea (*Ctenocephalides felis*), Human flea (*Pulex irritans*), Sticktight flea (*Echidnophaga gallinacea*), Cheops rat flea (*Xenopsylla cheopis*), Mole rat flea (*Leptopsylla segnis*), Europe rat flea (*Nosopsyllus fasciatus*), Yamato rat flea (*Monopsyllus anisus*), and the like.

Furthermore, other external parasites that can be controlled include, for example, lice such as Short-nosed cattle louse (*Haematopinus eurysternus*), Umajirami (*Haematopinus asini*), Hitsujijirami (*Dalmalinia ovis*), Ushihosojirami (*Linognathus vituli*), Pig louse (*Haematopinus suis*), Pubic louse (*Phthirus pubis*), and Head lice (*Pediculus capitis*), Body louse such as Inuhajirami (*Trichodectes canis*), and other blood-sucking diptera pest insects, such as Horsefly (*Tabanus trigonus*), Uainukaka (*Culicoides schultzei*), Tsumetogebuyu (*Simulium ornatum*), and the like. Also, internal parasites include, for example, lungworms, whipworms, nodular worms, gastric parasites, round worms, filiform insects and other nematodes, *Diphyllobothrium mansoni*, *Diphyllobothrium latum*, *Diphyllobothrium caninum*, *Taenia multiceps*, *Echinococcus granulosus*, and *Echinococcus multilocularis* and other cestodes, Schistosomiasis *japonica*, *Fasciola hepatica* and other trematodes, coccidium, malaria parasite, chounainikuhoushichu, *Toxoplasma gondii*, *Cryptosporidium* and other protozoans, etc.

Since an agricultural/horticultural insecticide that contains, as its active ingredient, an oxazepine compound or salt thereof expressed by General Formula (1) according to the present invention has a remarkable effect of controlling the aforementioned pest insects that damage paddy crops, field crops, fruit trees, vegetables, and other crops as well as flowers, it can be applied in or on nurseries, rice paddies, crop fields, fruit trees, vegetables, and other crops, flowers, etc., and their seeds, water in rice paddies, stems and leaves, soils and other cultivation carriers, etc., when pest insects are expected to generate, before pest insects generate, or when their generation is confirmed, and the agricultural/horticultural insecticide proposed by the present invention will achieve the specified effects. In particular, a preferred mode of use is one that utilizes the so-called penetration migration characteristics, which involves application to the soil at nurseries for crops, flowers, etc., soil around planting holes used for transplantation, plant roots, irrigation water, water used for hydroponic farming, etc., so that the compound proposed by the present invention will be absorbed through the soil, or from the roots without going through the soil.

Useful plants on which the agricultural/horticultural insecticide proposed by the present invention can be used are not limited in any way, and examples include grains (such as, rice, barley, wheat, rye, oats, corn, etc.), beans (soybeans, azuki beans, broad beans, peas, kidney beans, peanuts, etc.), fruit trees/fruits (apple, citrus, pear, grapes, peach, plum, yellow peach, walnuts, chestnuts, almonds, bananas, etc.), leafy/fruit vegetables (cabbage, tomatoes, spinach, broccoli, lettuce, onions, green onions (chieves, wakegi), bell peppers, eggplant, strawberries, peppers, okra, leeks etc.), root vegetables (carrots, potatoes, sweet potatoes, taro, daikon radish, turnips, lotus root, burdock, garlic, shallots, etc.), crops for processing (cotton, hemp, beets, hops, sugar cane, sugar beets, olives, gum, coffee, tobacco, tea, etc.), gourds (pumpkins, cucumbers, watermelon, oriental melons, melons, etc.), pasture grass (orchard grass, sorghum, timothy, clover, alfalfa, etc.), lawn (Korean lawn, bent grass, etc.), herbs and other ornamental crops (lavender, rosemary, thyme, parsley, pepper, ginger, etc.), flowers (chrysanthemums, roses, carnations, orchids, tulips, lilies, etc.), garden trees (ginkgo, cherry, Japanese laurel, etc.), forest trees (fir, Japanese spruce, pine, hiba, cedar, hinoki, eucalyptus, etc.) and others.

The aforementioned "plants" include plants to which resistance to isoxaflutole and other HPPD inhibitors, imazethapyr, thifensulfuron methyl, and other ALS inhibitors, glyphosate and other EPSP synthetic enzyme inhibitors, glufosinate and other glutamine synthetic enzyme inhibitors, sethoxydim and other acetyl CoA carboxylase inhibitors, and bromoxynil, dicamba, 2,4-D, and other herbicides, has been provided by traditional breeding methods or genetic modification engineering.

Examples of "plants" to which resistance has been provided by traditional breeding methods include rapeseed, wheat, sunflower, and rice resistant to imazethapyr and other imidazolinone ALS inhibitor-type herbicides, such as those currently sold under the product name Clearfield (registered trademark). Also, a soybean that has been made resistant to thifensulfuron methyl and other sulfonyl urea ALS inhibitor-type herbicides using a traditional breeding method is already available on the market under the product name STS Soybean. Similarly, SR Corn is one example of plants to which resistance to acetyl CoA carboxylase inhibitors, such as trione oxime, allyloxy phenoxy propionate and other herbicides, has been added using a traditional breeding method.

Also, plants to which resistance to acetyl CoA carboxylase inhibitors has been added are described in Proceedings of the National Academy of Sciences of the United States of America (Proc. Natl. Acad. Sci. USA), vol. 87, pp. 7175-7179 (1990), etc. Also, mutant acetyl CoA carboxylases resistant to acetyl CoA carboxylase inhibitors are reported in Weed Science, vol. 53, pp. 728-746 (2005), etc. and by introducing these mutant acetyl CoA carboxylase genes to plants via genetic modification engineering, or by introducing the mutation relating to the adding of resistance to plant acetyl CoA carboxylases, plants resistant to acetyl CoA carboxylase inhibitors can be created; and furthermore, by introducing a site-specific amino acid substitution mutation to plant acetyl CoA carboxylase genes, ALS genes, etc., which is done by introducing into plant cells a nucleic acid to which a base substitution mutation has been introduced using chimeraplasty (Gura T. 1999. Repairing the Genome's Spelling Mistakes. Science 285: 316-318), plants resistant to acetyl CoA carboxylase inhibitors, ALS inhibitors, etc., can be created, and the agricultural/horticultural insecticide proposed by the present invention can also be used on these plants.

Furthermore, toxins that manifest in genetically modified plants include, insecticidal proteins derived from *Bacillus cereus* and *Bacillus popilliae*; Cry1Ab, Cry1Ac, Cry1F, CrylFa2, Cry2Ab, Cry3A, Cry3Bb1, Cry9C and other δ-endotoxins, VIP1, VIP2, VIP3 or VIP3A and other insecticidal proteins derived from *Bacillus thuringiensis*; insecticidal proteins derived from nematodes; scorpion toxin, spider toxin, bee toxin, or insect-specific nerve toxin and other toxins produced in animals; filiform toxins; plant lectin; agglutinins; trypsin inhibitors, serin protease inhibitors, patatin, cystatin, papain inhibitors and other protease inhibitors; ricin, corn-RIP, abrin, luffin, saporin, bryodine and other ribosome inactivating proteins (RIP); 3-hydroxysteroid oxidase, ecdysteroid-UDP-glucosyl transferase, cholesterol oxidase and other steroid metabolic enzyme; ecdysone inhibitors; HMG-CoA reductase; sodium channel and calcium channel inhibitors and other ion channel inhibitors; young hormone esterase; diuretic hormone receptors; stilbene synthase; bi-benzyl synthase; chitinase; glucanase, etc.

Also, toxins that manifest in these genetically modified plants include hybrid toxins based on Cry1Ab, Cry1Ac, Cry1F, CrylFa2, Cry2Ab, Cry3A, Cry3Bb1, Cry9C, Cry34Ab, Cry35Ab and other δ-endotoxin proteins, VIP1, VIP2, VIP3, VIP3A and other insecticidal proteins, as well as partially defective toxins and modified toxins. Hybrid toxins are created by modification engineering, based on new combinations of different domains of these proteins. Among partially defective toxins, Cry1Ab whose amino acid sequence is partially defective is known. Modified toxins are natural toxins whose amino acid or acids is/are substituted.

Examples of these toxins, and modified plants capable of synthesizing these toxins, are described in EP-A-0 374 753, WO 93/07278, WO 95/34656, EP-A-0 427 529, EP-A-451 878, WO 03/052073, etc.

Toxins contained in these modified plants add resistance to plants, in particular, to coleoptera pest insects, hemiptera pest insects, diptera pest insects, lepidoptera pest insects and nematodes. The agricultural/horticultural insecticide proposed by the present invention may be combined or systematized with such technology.

To control various pest insects, the agricultural/horticultural insecticide proposed by the present invention may be used directly, or in a state diluted or suspended in water, etc., as appropriate, on plants where pest insects and nematodes are expected to generate, by an amount effective in controlling such pest insects and nematodes; to control pest insects and nematodes generating on fruit trees, grains, vegetables, etc., for example, it may be sprayed over stems and leaves, made into a solution agent in which seeds are soaked, prepared as powder to coat or otherwise treat seeds using Calper, etc., mixed into the entire layers of soil, applied in planting rows, mixed into bed soil, applied in cell seedlings, planting holes, around plant roots, in top dressing, rice boxes, on water surfaces, etc., or applied in soil, etc., to be absorbed through the roots. It may also be applied in nutrient solution in nutrient solution (hydroponic) cultivation, or used by means of smoking, tree trunk injection, etc.

Furthermore, the agricultural/horticultural insecticide proposed by the present invention may be used directly, or in a state diluted or suspended in water, etc., as appropriate, in locations where pest insects are expected to generate, by an amount effective in controlling such pest insects, for example, it may be sprayed over stored-grain pest insects, house pest insects, hygiene pest insects, forest pest insects, etc., and may also be applied to residential construction materials, smoked, used as bait, etc.

Methods for treating seeds include, for example, a method to soak the seeds in the product in liquid form or in a liquid prepared from the product in solid form, with or without dilution, and let the reagent permeate in the seeds; a method to mix and powder-coat the product in solid form or liquid form with/on the seeds to cause the reagent to attach to the surface of the seeds; a method to mix the reagent with resin, polymer, or other adhesive carrier and then coat the mixture on the seeds; and a method to spray a reagent near the seeds when they are planted.

"Seeds" treated by these methods refer to initial forms of plants to be cultivated for propagation of plants, where examples, other than seeds, include, bulbs, tubers, seed potatoes, stock sprouts, propagule, scaly bulbs, and plant forms used for vegetative propagation for the purpose of grafting.

When applying a method of use of the present invention, "soil" or "cultivation carriers" for plants refers to a support on which to cultivate a crop, or specifically a support in which to grow roots, and its material, which is not limited in any way so long a plant can grow in it, may be a so-called soil, nursery mat, water, etc., or specifically it may be, for example, sand, pumice, vermiculite, diatomaceous earth, agar, gel-like substance, polymeric substance, rock wool, glass wool, wood chips, bark, etc.

Methods for spraying over stems and leaves of crops or over stored-grain pest insects, house pest insects, hygiene pest insects, forest pest insects, etc., include a method to spray the product in emulsion form, flowable form, or other liquid form, or in wettable powder form, water-dispersible granular form, or other solid form that has been diluted in water as deemed appropriate; a method to spray the product in powder form; smoking; or the like.

Methods for application to soil include, for example, a method to apply the product in liquid form with or without dilution in water, to roots of plant forms, nursery beds, etc.; a method to spray the product in granular form over roots of plant forms, nursery beds, etc.; a method to spray the product in powder form, wettable powder form, water-dispersible granular form, granular form, etc., before seeding or transplanting, and mix it with the entire soil; and a method to spray the product in powder form, wettable powder form, water-dispersible granular form, granular form, etc., to planting holes, planting rows, etc., before seeding or before planting of plant forms, etc.

Concerning methods for application to rice nursery beds, the product may be in different forms depending on the timing of application, such as the seeding stage, vegetation stage, transplantation stage, etc., where it may be applied in such forms as powder, water-dispersible granules, granules, etc. The product may also be mixed with cultivation soil, in the form of mixing of cultivation soil with powder, water-dispersible granules, granules, etc., such as mixing with bed soil, mixing with cover soil, mixing with the entire cultivation soil, etc. Cultivation soil may be simply layered with various forms of the product.

On methods for application to rice paddies, the product in jumbo pack form, pack form, granular form, water-dispersible granular form or other solid form, or in flowable form, emulsion form, or other liquid form, is normally sprayed over rice paddies that are flooded with water. In addition, when planting rice seedlings the product in an appropriate form may be directly, or mixed with fertilizer first, sprayed over or injected into soil. Also, the reagent in emulsion form, flowable form, etc., may be used at water gates, irrigation systems or other sources of water, etc., that flows into rice paddies, so that it is applied with the supply of water and labor can be saved.

With field crops, cultivation carriers, etc., in close proximity of seeds and plant forms can be treated in the seeding stage through nursery stage. With plants whose seeds are directly sown on crop fields, ideally the product is directly applied to seeds or to plant roots during cultivation. The product may be sprayed in granular form, or the product in liquid form with or without dilution in water may be applied through irrigation, etc. It is also desirable to mix the product in granular form with a cultivation carrier before seeding, and then perform seeding.

For treatment in the seeding and nursery stage of plants to be cultivated for transplantation, desirably the seeds are treated directly or the product in liquid form is applied through irrigation to, or the product in granular form is sprayed over, nursery beds. It is also desirable to apply the product in granular form to planting holes at the time of final planting, or mix it with the cultivation carrier near the transplanting destination.

The agricultural/horticultural insecticide proposed by the present invention is generally formed into shapes convenient for use, according to normal methods of formulation of agricultural chemicals.

To be specific, an oxazepine compound or salt thereof expressed by General Formula (1) according to the present invention may be blended into an appropriate inert carrier, by an appropriate ratio, together with an auxiliary agent, if necessary, and dissolved, separated, suspended, mixed, impregnated, adsorbed or attached, and formulated into an appropriate form such as a suspension, emulsion, liquid, wettable powder, water-dispersible granules, granules, powder, tablets, pack, etc., for use.

The composition of the present invention (agricultural/horticultural insecticide or zoobiotic parasite control agent) may contain, in addition to its active ingredient, those additive ingredients normally used in agricultural chemicals or zoobiotic parasite control agent, if necessary. Those additive ingredients include solid carriers, liquid carriers, and other carriers, surface active agents, dispersants, wetting agents, binders, tackifiers, thickening agents, coloring agents, extenders, spreading agents, anti-freeze agents, anti-caking agents, disintegrating agents, stabilizing agents, etc. In addition to the above, preservatives, plant pieces, etc., may also be used as additive ingredients, if necessary. Any of these additive ingredients may be used alone or two or more types may be combined.

Solid carriers include, for example, quartz, clay, kaolinite, pyrophyllite, sericite, talc, bentonite, acid clay, attapulgite, zeolite, diatomaceous earth and other natural minerals, calcium carbonate, ammonium sulfate, sodium sulfate, potassium chloride and other inorganic salts, synthetic silicic acid, synthetic silicate, starch, cellulose, plant powders (such as sawdust, coconut shell, corn cob, tobacco stem, etc.) and other organic solid carriers, polyethylene, polypropylene, polyvinylidene chloride and other plastic carriers, urea, inorganic hollows, plastic hollows, fumed silica (white carbon), etc. Any of these may be used alone or two or more types may be combined.

Liquid carriers include, for example, alcohols such as methanol, ethanol, propanol, isopropanol, butanol and other monohydric alcohols, ethylene glycol, diethylene glycol, propylene glycol, hexylene glycol, polyethylene glycol, polypropylene glycol, glycerin, and other polyhydric alcohols, propylene glycol ether and other polyhydric alcohol compounds, acetone, methyl ethyl ketone, methyl isobutyl ketone, diisobutyl ketone, cyclohexanone and other ketones, ethyl ether, dioxane, ethylene glycol monoethyl ether, dipropyl ether, THF, and other ethers, normal paraffin, naphthene, isoparaffin, kerosene, mineral oil and other fatty acid hydrocarbons, benzene, toluene, xylene, solvent naphtha, alkyl naphthalene and other aromatic hydrocarbons, dichloromethane, chloroform, carbon tetrachloride and other halogenated hydrocarbons, ethyl acetate, diisopropyl phthalate, dibutyl phthalate, dioctyl phthalate, dimethyl adipate and other esters, γ-butyrolactone and other lactones, dimethyl formamide, diethyl formamide, dimethyl acetamide, N-alkyl pyrrolidinone and other amides, acetonitrile and other nitriles, dimethyl sulfoxide and other sulfur compounds, soybean oil, rapeseed oil, cotton seed oil, castor oil and other vegetable oils, water, etc. Any of these may be used alone or two or more types may be combined.

Surface active agents used as dispersants and wetting agents include, for example, sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether formalin condensation product, polyoxyethylene polyoxypropylene block copolymer, polystyrene polyoxyethylene block polymer, alkyl polyoxyethylene polypropylene block copolymer ether, polyoxyethylene alkyl amine, polyoxyethylene fatty acid amide, polyoxyethylene fatty acid bisphenyl ether, polyalkylene benzyl phenyl ether, polyoxyalkylene styryl phenyl ether, acetylene diol, polyoxy alkylene added acetylene diol, polyoxyethylene ether-type silicone, ester-type silicone, fluorine surface active agents, polyoxyethylene castor oil, polyoxyethylene hardened castor oil and other non-ionic surface active agents, alkyl sulfate, polyoxyethylene alkyl ether sulfate, polyoxyethylene alkyl phenyl ether sulfate, polyoxyethylene styryl phenyl ether sulfate, alkyl benzene sulfonate, alkyl aryl sulfonate, lignin sulfonate, alkyl sulfosuccinate, naphthalene sulfonate, alkyl naphthalene sulfonate, salt of formalin condensation product of naphthalene sulfonic acid, salt of formalin condensation product of alkyl naphthalene sulfonate, fatty acid salt, polycarbonate, polyacrylate, N-methyl-fatty acid sarcosinate, resin acid salt, polyoxyethylene alkyl ether phosphate, polyoxyethylene alkyl phenyl ether phosphate and other anionic surface active agents, lauryl amine hydrochloride, stearyl amine hydrochloride, oleyl amine hydrochloride, stearyl amine acetate, stearyl aminopropyl amine acetate, alkyl trimethyl ammonium chloride, alkyl dimethyl benzalkonium chloride and other alkyl amine salts and other cationic surface active agents, amino acid-type or betaine-type and other ampholytic surface active agents, etc. Any of these surface active agents may be used alone or two or more types may be combined.

Binders and tackifiers include, for example, carboxy methylcellulose and salt thereof, dextrin, water-soluble starch, xanthan gum, guar gum, sucrose, polyvinyl pyrrolidone, gum arabic, polyvinyl alcohol, polyvinyl acetate, sodium polyacrylate, polyethylene glycol with an average molecular weight of 6000 to 20000, polyethylene oxide with an average molecular weight of 100000 to 5000000, phospholipids (such as cephaline, lecithin, etc.), cellulose powder, dextrin, processed starch, polyamino carboxylic chelate compound, cross-linked polyvinyl pyrrolidone, maleate and styrene copolymer, (meth)acrylate copolymer, half ester of polyhydric alcohol-based polymer and dicarboxylic anhydride, water-soluble salt of polystyrene sulfonate, paraffin, terpene, polyamide resin, polyacrylate, polyoxyethylene, wax, polyvinyl alkyl ether, alkyl phenol formalin condensation product, synthetic resin emulsion, etc.

Thickening agents include, for example, xanthan gum, guar gum, diutan gum, carboxy methyl cellulose, polyvinyl pyrrolidone, carboxy vinyl polymer, acrylic polymers, starch compounds, polysaccharides and other water-soluble polymers, highly pure bentonite, fumed silica (white carbon) and other inorganic fine powders, etc.

Coloring agents include, for example, iron oxide, titanium oxide, Prussian blue and other inorganic pigments, alizarin dyes, azo dyes, metal phthalocyanine dyes and other organic dyes, etc.

Anti-freeze agents include, for example, ethylene glycol, diethylene glycol, propylene glycol, glycerin and other polyhydric alcohols, etc.

Auxiliary agents to prevent caking or promote disintegration include, for example, starch, alginic acid, mannose, galactose and other polysaccharides, polyvinyl pyrrolidone, fumed silica (white carbon), ester gum, petroleum resin, sodium tripolyphosphate, sodium hexametaphosphate, stearate metal salt, cellulose powder, dextrin, methacrylate ester copolymer, polyvinyl pyrrolidone, polyamino carboxylic chelate compound, sulfonated styrene-isobutylene-maleate anhydride copolymer, starch-polyacrylonitrile graft copolymer, etc.

Stabilizing agents include, for example, zeolite, raw lime, magnesium oxide and other drying agents, phenol compounds, amine compounds, sulfur compounds, phosphate compounds and other anti-oxidants, salicylate compounds, benzophenone compounds and other UV absorbents, etc.

Preservatives include, for example, potassium sorbate, 1,2-benzothiazoline-3-one, etc.

Furthermore, functional spreading agents, piperonyl butoxide and other metabolic breakdown inhibitors and other activity enhancing agents, BHT and other anti-oxidants, UV absorbents and other auxiliary agents may also be used, as necessary.

The blending ratio of the active ingredient compound may be increased or decreased as necessary, to a level selected as deemed appropriate in a range of 0.01 to 90 parts by weight relative to 100 parts by weight of the agricultural/horticultural insecticide proposed by the present invention. In the case of powder, granules, emulsion or wettable powder, for example, 0.01 to 50 parts by weight (0.01 to 50% by weight relative to the total weight of the agricultural/horticultural insecticide) is appropriate.

How much the agricultural/horticultural insecticide proposed by the present invention is used varies depending on various factors, such as purpose, pest insect to be controlled, condition of growth of the crop, trend of generation of the pest insect, weather, environmental conditions, form of the product, application method, application location, application timing, etc.; however, a desired amount of the active ingredient compound may be selected as deemed appropriate in a range of 0.001 g to 10 kg, or preferably 0.01 g to 1 kg, per 10 ares.

The agricultural/horticultural insecticide proposed by the present invention may be mixed with other agricultural/horticultural insecticide, miticides, nematicides, bactericides, biological agrochemicals, etc., for the purpose of expanding the scope of pest insects to be controlled and timings at which they can be controlled, or for reducing the amount of chemical, or it may be mixed with herbicides, plant growth controlling agents, fertilizers, etc., depending on the application location.

Examples of other agricultural/horticultural insecticides, miticides, nematicides used for the aforementioned purposes include, among others, 3,5-xylyl methylcarbamate (XMC), *Bacillus thuringiensis aizawai, Bacillus thuringiensis israelensis, Bacillus thuringiensis* japonensis, *Bacillus thuringiensis* kurstaki, *Bacillus thuringiensis tenebrionis, Bacillus thuringiensis*-produced crystal protein toxins, BPMC, Bt toxin insecticidal compounds, CPCBS (chlorfenson), DCIP (dichlorodiisopropyl ether), D-D (1,3-Dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, acynonapyr, azinphos-methyl, acequinocyl, acetamiprid, acetoprole, acephate, abamectin, afidopyropen, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isocycloseram, isofenphos, isoprocarb (MIPC), epsilon-metofluthrin, epsilon-momfluorothrin, ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxazosulfyl, oxamyl, oxydemeton-methyl, oxydeprofos (ESP), oxibendazole, oxfendazole, Potassium oleate, sodium oleate, cadusafos, kappa-bifenthrin, cartap, carbaryl, carbosulfan, carbofuryl, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, chloroprallethrin, dicofol, salithion, cyanophos (CYAP), diafenthiuron, diamidafos, cyantraniliprole, theta-cypermethrin, dienochlor, cyetpyrafen, cyenopyrafen, dioxabenzofos, diofenolan, sigma-cypermethrin, cyclobutrifluram, dichlofenthion (ECP), cycloprothrin, dichlorvos (DDVP), dicloromezotiaz, disulfoton, dinotefuryl, cyhalodiamide, cyhalothrin, cyphenothrin, cyfluthrin, diflubenzuron, cyflumetofen, diflovidazin, cyhexatin, cypermethrin, dimethylvinphos, dimethoate, dimpropyridaz, dimefluthrin, silafluofen, cyromazine, spinetoram, spinosad, spirodiclofen, spirotetramat, spiropidion, spiromesifen, sulfluramid, sulprofos, sulfoxaflor, zeta-cypermethrin, diazinon, tau-fluvalinate, dazomet, thiacloprid, thiamethoxam, tioxazafen, thiodicarb, thiocyclam, thiosultap, thiosultap-sodium, thionazin, thiometon, tyclopyrazoflor, deet, dieldrin, tetrachlorantraniliprole, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nicofluprole, nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, pyflubumide, bifenazate, bifenthrin, pymetrozine, pyraclorfos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, formetanate, butathiofos, buprofezin, furathiocarb, prallethrin, fluacrypyrim, fluazaindolizine, fluazinam, fluazuron, fluensulfone, fluxametamide, flucycloxuron, flucythrinate, fluvalinate, flupyrazofos, flupyrimin, flufenerim, flufenoxuron, flufenzine, flufenprox, fluproxyfen, flubrocythrinate, fluhexafon, flubendiamide, flupentiofenox, flumethrin, flurimfen, prothiofos, protrifenbute, flonicamid, propaphos, propargite (BPPS), profenofos, broflanilide, profluthrin, propoxur (PHC), flometoquin, alpha-bromadiolone, bromopropylate, beta-cyfluthrin, hexaflumuron, hexythiazox, heptafluthrin, heptenophos, permethrin, benclothiaz, bendiocarb, benzpyrimoxan, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, rescalure, resmethrin, lepimectin, rotenone, levamisol hydrochloride, fenbutatin oxide, morantel tartarate, methyl bromide, cyhexatin, calcium cyanamide, calcium polysulfide, sulfur, and nicotine-sulfate.

Examples of agricultural/horticultural fungicides used for similar purposes include, among others aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isofetamid, isoflucypram, isoprothiolane, ipconazole, ipfentrifluconazole, ipflufenoquin, iprodione, iprovalicarb, iprobenfos, imazalil, iminoctadine, iminoctadine-albesilate, iminoctadine-triacetate, imibenconazole, inpyrfluxam, uniconazole, uniconazole-P, echlomezole, edifenphos, etaconazole, ethaboxam, ethirimol, etem, ethoxyquin, etridiazole, enestroburin, enoxastrobin, epoxiconazole, oxadixyl, oxathiapiprolin, oxycarboxin, copper-8-quinolinolate, oxytetracycline, copper-oxinate, oxpoconazole, oxpoconazole-fumarate, oxolinic acid, octhilinone, ofurace, orysastrobin, soil sterilizers such as metam-sodium, kasugamycin, carbamorph, carpropamid, carbendazim, carboxin, carvone, quinazamid, quinacetol, quinoxyfen, quinofumelin, chinomethionat, captafol, captan, kiralaxyl, quinconazole, quintozene, guazatine, cufraneb, cuprobam, coumoxystrobin, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, dichlobentiazox, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thioquinox, thiochlorfenphim, thiophanate, thiophanate-methyl, thicyofen, thifluzamide, thiram, decafentin, tecnazene, tecloftalam, tecoram, tetraconazole, debacarb, dehydroacetic acid, tebuconazole, tebufloquin, dodicin, dodine, Dodecylbenzenesulphonic acid bisethylenediamine copper [II] salt (DBEDC), dodemorph, drazoxolon, triadimenol, triadimefon, triazbutil, triazoxide, triamiphos, triarimol, trichlamide, triclopyricarb, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, picarbutrazox, bixafen, picoxystrobin, picobenzamide, pydiflumetofen, bithionol, bitertanol, hydroxyisoxazole, hydroisoxazole-potassium, binapacryl, biphenyl, piperalin, hymexazol, pyraoxystrobin, pyracarbolid, pyraclostrobin, pyrazophos, pyrapropoyne, pyrametostrobin, pyriofenone, pyridinitril, pyrisoxazole, pyridachlometyl, pyrifenox, pyribencarb, pyriminostrobin, pyrimethanil, pyroxychlor, pyroxyfur, pyroquilon, vinclozolin, famoxadone, fenapanil, fenamidone, fenaminosulf, fenaminstrobin, fenarimol, fenitropan, fenoxanil, ferimzone, ferbam, fentin, fenpiclonil, fenpicoxamid, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluindapyr, fluoxastrobin, fluoxapiprolin, fluotrimazole, fluopicolide, Fluopimomide, fluopyram, fluoroimide, furcarbanil, fluxapyroxad, fluquinconazole, furconazole, furconazole-cis, fludioxonil, flusilazole, flusulfamide, flutianil, flutolanil, flutriafol, flufenoxystrobin, furfural, flubeneteram, furmecyclox, flumetover, flumorph, proquinazid, prochloraz, procymidone, prothiocarb, prothioconazole, pronitridine, propamocarb, propiconazole, propineb, furophanate, probenazole, bromuconazole, florylpicoxamid, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipromid, mandestrobin, myclozolin, myclobutanil, mildiomycin, milneb, mecarbinzid, methasulfocarb, metazoxolon, metam, metam-sodium, metalaxyl, metalaxyl-M, metiram, methyl isothiocyanate, mepthyldinocap, Metyltetraprole, metconazole, metsulfovax, methfuroxam, metominostrobin, metrafenone, mepanipyrim, mefenoxam, mefentrifluconazole, meptyldinocap, mepronil, mebenil, iodomethane, rabenzazole, benzalkonium chloride, basic copper chloride, basic copper sulfate, inorganic bactericides such as silver, sodium hypochlorote, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as 8-hydroxy quinoline copper (oxine copper), zinc sulfate, and copper sulfate pentahydrate.

Similarly, examples of herbicides include, among others, 1-Naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, iofensulfuron, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalflralin, ethiolate, ethychlozate ethyl, ethidimuron, etinofen, ethephon, ethoxysulfuron, ethoxyfen, etnipromid, ethofumesate, etobenzanid, epyrifenacil, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, clacyfos, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, coransulam, chloranocryl, chloramben, cloransulam-methyl, chloridazon, chlorimuron, chlorimuron-ethyl, chlorsulfuron, chlorthal, chlorthiamid, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, cyclopyranil, cyclopyrimorate, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimesulfazet, dimethachlor, dimidazon, dimethametryn, dimethenamid, simetryn, simeton, dimeperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, tiafenacil, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetflupyrolimet, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, triafamone, tri-allate, trietazine, tricamba, triclopyr, tridiphane, tritac, tritosulfuron, trifludimoxazin, triflusulfuron, triflusulfuron-methyl, trifluralin, trifloxysulfuron, tripropindan, tribenuron-methyl, tribenuron, trifop, trifopsime, trimeturon, tolpyralate, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, halauxifen, haloxyfop, haloxyfop-P, haloxyfop-methyl, halosafen, halosulfuron, halosulfuron-methyl, bixlozone, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenquinotrione, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, florpyrauxifen, hexachloroacetone, hexazinone, pethoxamid, benazolin, penoxsulam, pebulate, beflubutamid, beflubutamid-M, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, lancotrione, linuron, rimsulfuron, lenacil, rhodethanil, calcium peroxide, and methyl bromide.

Also, similar effects can be expected by mixing with biological agrochemicals, such as nuclear polyhedrosis virus (NPV), granulosis virus (GV), cytoplasmic polyhedrosis virus (CPV), entomopoxi virus (EPV) and other virus agents, *Monacrosporium phymatophagum*, *Steinernema carpocapsae*, *Steinernema kushidai*, *Pasteuria penetrans*, and other microbial agrochemicals used as insecticides or nematicides, *Trichoderma lignorum*, *Agrobacterium radiobactor*, *Erwinia carotovora*, *Bacillus subtilis*, and other microbial agrochemicals used as bactericides, *Xanthomonas campestris* and other biological agrochemicals used as herbicides, and the like.

Furthermore, it is also possible to mix with such biological agrochemicals as Onshitsutsuyakobachi (*Encarsia formosa*), Koremanaburabachi (*Aphidius colemani*), Shokugatamabae (*Aphidoletes aphidimyza*), Isaeahimekobachi (*Diglyphus isaea*), Hamogurikomayubachi (*Dacnusa sibirica*), Chirikaburidani (*Phytoseiulus persimilis*), Kukumerisukaburidani (*Amblyseius cucumeris*), Namihimehanakamemushi (*Orius sauteri*), and other natural predators, *Beauveria brongniartii* and other microbial agrochemicals, (Z)-10-tetradecenyl=acetate, (E,Z)-4,10-tetradecadienyl=acetate, (Z)-8-dodecenyl=acetate, (Z)-11-tetradecenyl=acetate, (Z)-13-icosen-10-one, 14-methyl-1-octadecene, and other pheromone agents.

EXAMPLES

Representative examples of the present invention are shown below, but the present invention is not limited to these examples.

Manufacture Example 1

Manufacturing of 9-(methoxymethyl)-2-(pyridin-3-yl)-2H-pyrazolo[3,4-f]pyrido[2,3-b][1,4]oxazepine-10(9H)-one (Compound No. 1-1)

[chem 5]

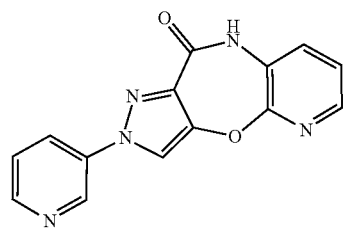

-continued

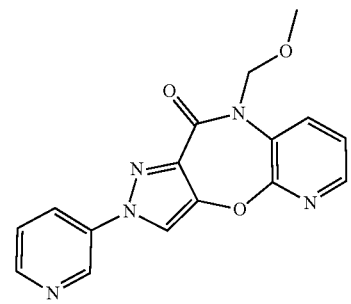

Sodium hydride (1.75 g, 43.8 mmol) was added to dry THF/dry DMF (240 mL/60 mL) solution of 2-(pyridin-3-yl)-2H-pyrazolo[3,4-f]pyrido[2,3-b][1,4]oxazepine-10(9H)-one (8.16 g, 29.2 mmol) at 0° C. and stirred for 30 minutes at room temperature. The reaction solution was cooled again to 0° C., after which chloromethylmethyl ether (4.14 g, 49.6 mmol) was added thereto, and the mixture was stirred for 4 hours at room temperature. The reaction solution was poured into aqueous solution of saturated ammonium chloride (400 mL), allowed to stand overnight. The unreacted raw ingredients deposited were filtered off using a Buchner funnel. The filtrate was extracted with ethyl acetate/THF (ca. 1/1), washed with water and saturated salt water one by one, and the organic layer was dried using anhydrous magnesium sulfate, and then vacuum concentrated. The residue was refined by NH silica gel column chromatography, the obtained crystal was washed with ethyl acetate, and then filtered out, to obtain the title compound (4.36 g, 13.5 mmol).

Yield: 46%

Physical property: melting point 209-210° C.

Manufacture Example 2

Manufacturing of 9-(methoxymethyl)-2-(pyridin-3-yl)-2H-pyrazolo[3,4-f]pyrido[2,3-b][1,4]oxazepine-10(9H)-one (Compound No. 1-1)

[chem 6]

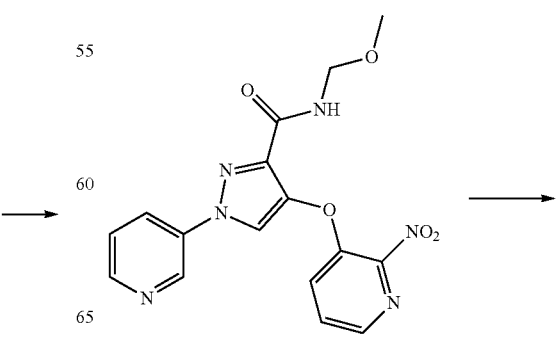

-continued

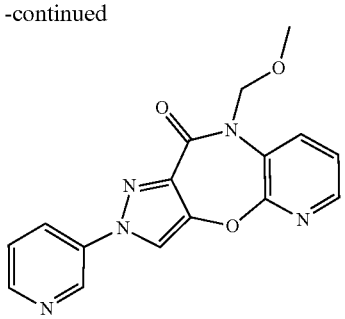

Potassium carbonate (2.00 g, 14.0 mmol) was added to acetonitrile (45 mL) solution of N-(methoxymethyl)-4-((2-nitropyridin-3-yl)oxy)-1-(pyridin-3-yl)-1H-pyrazole-3-carboxamide (2.00 g, 14.0 mmol), and stirred for 2 hours under heating to reflux. The reaction solution was filtered out using Celite in a state maintaining heat, and the filtrate was vacuum concentrated. Chloroform (15 mL) and aqueous solution of saturated ammonium chloride (1 mL) were added to the residue obtained, and the organic layer was extracted with chloroform, after which the organic layer was washed with saturated salt water. The organic layer was dried using anhydrous sodium sulfate, and then vacuum concentrated to obtain the title compound (0.71 g, 2.20 mmol).
Yield: 81%
Physical property: melting point 209-210° C.

Manufacture Reference Example 1

Manufacturing of ethyl (E)-4-chloro-3-oxo-2-(2-(pyridin-3-yl)hydrazono) butanoate

[chem 7]

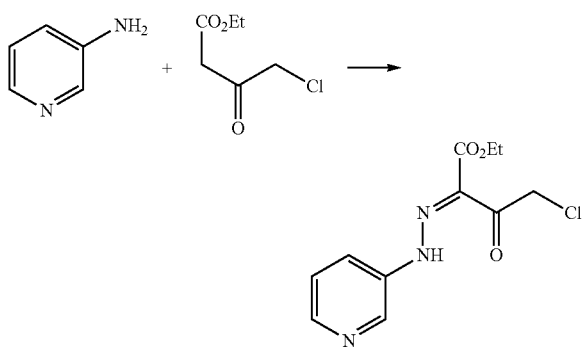

3-Aminopyridine (7.52 g, 80.0 mmol) was added to 6N-hydrochloric acid (27 mL, 160 mmol). Into this solution, aqueous solution (40 mL) of sodium nitrite (5.52 g, 80.0 mmol) was dripped by keeping the temperature at 3° C. or below, and the mixture was stirred for 20 minutes. Thereafter, ethyl 4-chloroaceto acetate (13.2 g, 80.0 mmol), ethyl acetate (30 mL), sodium acetate (15.0 g, 183 mmol) were added, and stirred for 1 hour at 0° C. Ethyl acetate and water were added to the reaction solution, and the organic layer was extracted with ethyl acetate, after which the organic layer was washed with saturated salt water, dried using anhydrous magnesium sulfate, and then vacuum concentrated. The residue was refined by silica gel column chromatography, to obtain the title compound (17.8 g, 66.0 mmol).

Yield: 82%
Physical property: $^1$H-NMR (CDCl$_3$/TMS, ppm) δ 13.02 (1H, s), 8.67-8.63 (1H, m), 8.47-8.44 (1H, m), 7.75-7.69 (1H, m), 7.41-7.35 (1H, m), 4.69 (2H, m), 4.41 (2H, q), 1.42 (3H, t)

Manufacture Reference Example 2

Manufacturing of ethyl 4-hydroxy-1-(pyridin-3-yl)-1H-pyrazole-3-carboxylate

[chem 8]

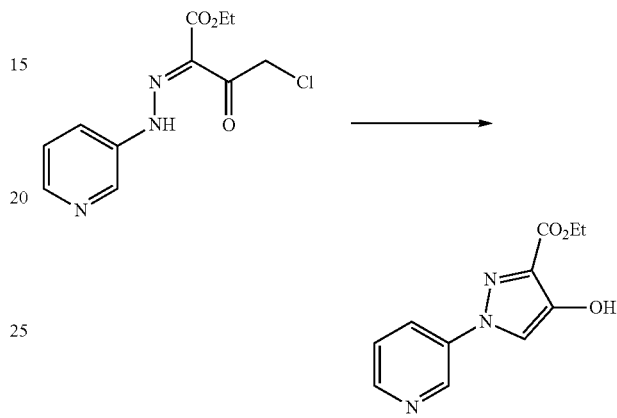

Tert-butoxy potassium (7.84 g, 70.0 mmol) was added to THF (70 mL) solution of ethyl (E)-4-chloro-3-oxo-2-(2-(pyridin-3-yl)hydrazono) butanoate (17.0 g, 63.0 mmol) at 0° C. and stirred for 1 hour at room temperature. Aqueous solution of saturated ammonium chloride was added to the reaction solution and then the organic layer was extracted with ethyl acetate, after which the organic layer was washed with saturated salt water, dried using anhydrous magnesium sulfate, and then vacuum concentrated. The obtained crystal was washed with hexane/ethyl acetate and then filtered out, to obtain the title compound (12.0 g, 51.4 mmol).
Yield: 82%
Physical property: melting point 135-137° C.

Manufacture Reference Example 3

Manufacturing of ethyl 4-((3-nitropyridin-2-yl)oxy)-1-(pyridin-3-yl)-1H-pyrazole-3-carboxylate

[chem 9]

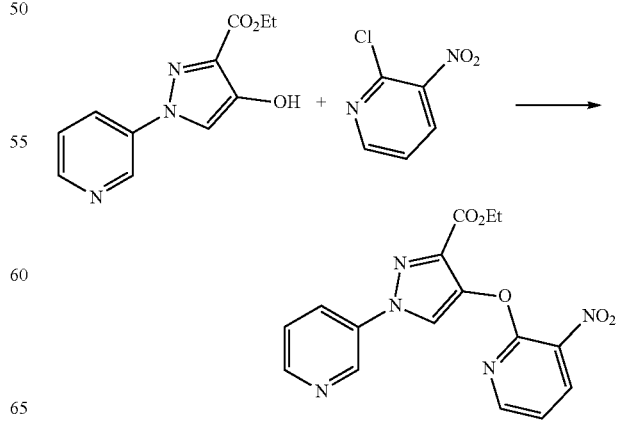

2-Chloro-3-nitropyridine (14.9 g, 94.3 mmol) and potassium carbonate (16.6 g, 120 mmol) were added to acetonitrile solution (400 mL) of ethyl 4-hydroxy-1-(pyridin-3-yl)-1H-pyrazole-3-carboxylate (20.0 g, 85.8 mmol), and stirred for 1 hour under heating to reflux. The reaction solution was returned to room temperature, and then filtered out using Celite, and the filtrate was vacuum concentrated. The obtained crystal was washed with hexane/MTBE and then filtered out to obtain the title compound (29.3 g, 82.4 mmol).

Yield: 96%

Physical property: melting point 171-173° C.

Manufacture Reference Example 4

Manufacturing of ethyl 4-((3-aminopyridin-2-yl)oxy)-1-(pyridin-3-yl)-1H-pyrazole-3-carboxylate

[chem 10]

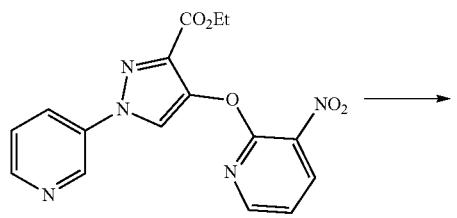

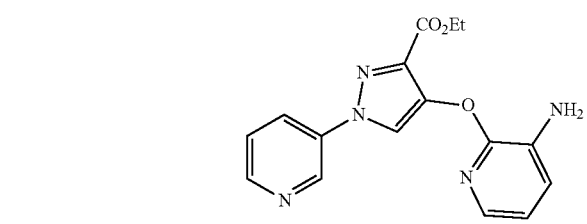

Ammonium chloride (2.20 g, 41.2 mmol) and electrolytic iron powder (23.0 g, 412 mmol) were added to ethanol/water (300 mL/150 mL) solution of ethyl 4-((3-nitropyridin-2-yl)oxy)-1-(pyridin-3-yl)-1H-pyrazole-3-carboxylate (29.3 g, 82.4 mmol), and stirred for 1 hour under heating to reflux. The reaction solution was returned to room temperature, and then filtered out using Celite, and the filtrate was vacuum concentrated. Ethyl acetate and water were added to this solution and an organic layer was extracted with ethyl acetate, after which the organic layer was washed with saturated salt water, dried using anhydrous magnesium sulfate, and then vacuum concentrated. The obtained crystal was washed with hexane/MTBE and then filtered out to obtain the title compound (25.2 g, 77.5 mmol).

Yield: 94%

Physical property: melting point 144-145° C.

Manufacture Reference Example 5

Manufacturing of 2-(pyridin-3-yl)-2H-pyrazolo[3,4-f]pyrido[2,3-b][1,4]oxazepine-10(9H)-one

[chem 11]

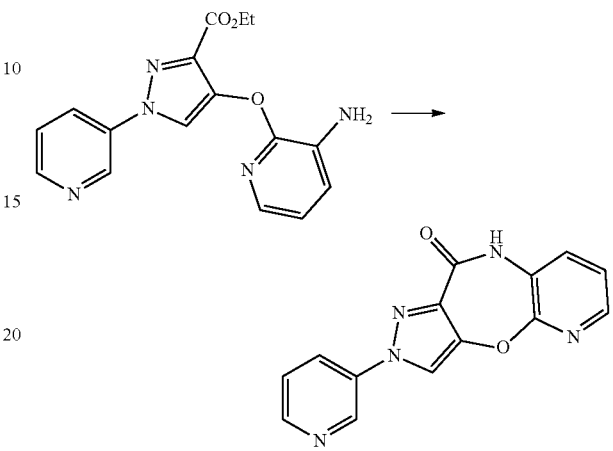

Tert-butoxy potassium (9.56 g, 80.9 mmol) was added to THF (460 mL) solution of ethyl 4-((3-aminopyridin-2-yl)oxy)-1-(pyridin-3-yl)-1H-pyrazole-3-carboxylate (18.8 g, 57.8 mmol) at 0° C., and stirred for 1 hour at the same temperature. The reaction solution was poured into aqueous solution of saturated ammonium chloride (600 mL), and the mixed solution was vacuum concentrated and the solvent was distilled off. This aqueous suspension was filtered out using a Buchner funnel, and the crystal filtered out was washed with water and dried by a forced air dryer. The obtained crystal was washed with ethyl acetate and then filtered out to obtain the title compound (14.2 g, 50.8 mmol).

Yield: 88%

Physical property: melting point >300° C.

Manufacture Reference Example 6

Manufacturing of 4-hydroxy-1-(pyridin-3-yl)-1H-pyrazole-3-carboxamide

[chem 12]

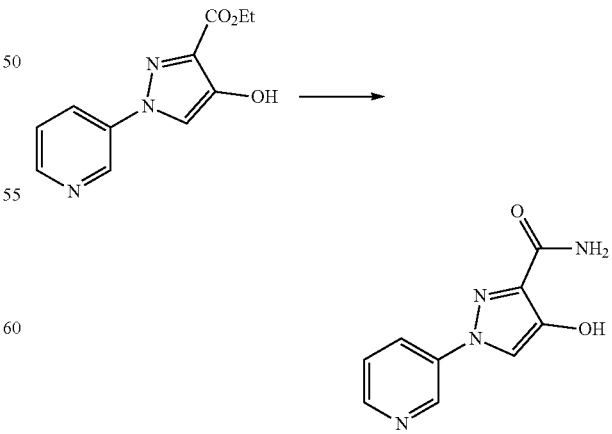

28% Aqueous ammonia (20 mL) was added to ethanol (50 mL) solution of ethyl 4-hydroxy-1-(pyridin-3-yl)-1H-pyrazole-3-carboxylate (10.0 g, 42.9 mmol), and stirred for 3 hours under heating to reflux. During reaction, 28% aqueous ammonia was added in 10 mL portions every hour, and 50 mL of 28% aqueous ammonia was used in total. The reaction solution was returned to room temperature, and then vacuum concentrated. The obtained crystal was washed with ethyl acetate and then filtered out to obtain the title compound (9.13 g, 44.5 mmol).
Yield: quantitative
Physical property: melting point 275-278° C.

Manufacture Reference Example 7

Manufacturing of 4-((2-nitropyridin-3-yl)oxy)-1-(pyridin-3-yl)-1H-pyrazole-3-carboxamide

[chem 13]

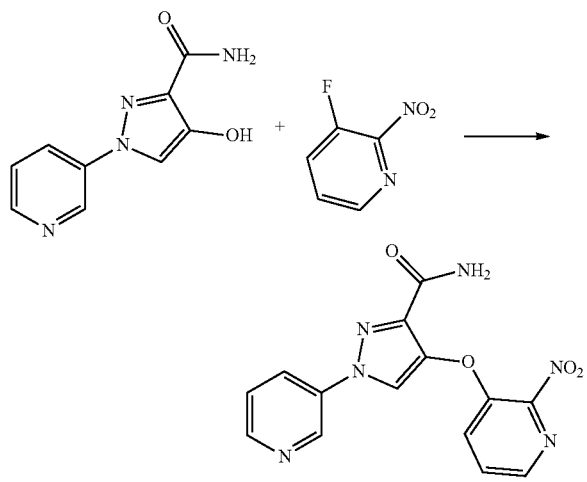

Potassium carbonate (5.30 g, 38.1 mmol) and 3-fluoro-2-nitropyridine (2.00 g, 14.0 mmol) were added to acetonitrile (65 mL) solution of 4-hydroxy-1-(pyridin-3-yl)-1H-pyrazole-3-carboxamide (2.60 g, 12.7 mmol), and stirred for 1 hour under heating to reflux. The reaction solution was filtered out using Celite in a state maintaining heat, and the filtrate was vacuum concentrated. The obtained crystal was washed with ethyl acetate and then filtered out to obtain the title compound (2.60 g, 8.00 mmol).
Yield: 63%
Physical property: melting point 179° C.

Manufacture Reference Example 8

Manufacturing of N-(hydroxymethyl)-4-((2-nitropyridin-3-yl)oxy)-1-(pyridin-3-yl)-1H-pyrazole-3-carboxamide

[chem 14]

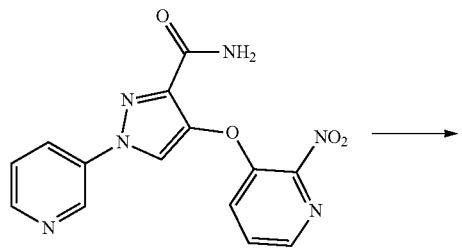

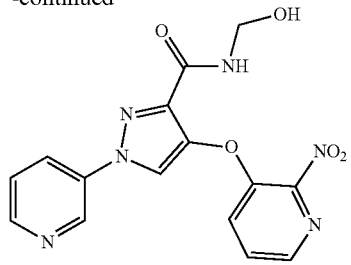

Potassium carbonate (0.11 g, 0.80 mmol) and 37% formalin (16 mL) were added to DMF (20 mL) solution of 4-((2-nitropyridin-3-yl)oxy)-1-(pyridin-3-yl)-1H-pyrazole-3-carboxamide (2.60 g, 8.00 mmol), and stirred for 3.5 hours at room temperature. Water (40 mL) was added to the reaction solution and stirred for 5 minutes. The crystal produced was filtered out and then washed with MTBE to obtain the title compound (2.50 g, 7.00 mmol).
Yield: 87%
Physical property: melting point 192° C.

Manufacture Reference Example 9

Manufacturing of N-(methoxymethyl)-4-((2-nitropyridin-3-yl)oxy)-1-(pyridin-3-yl)-1H-pyrazole-3-carboxamide

[chem 15]

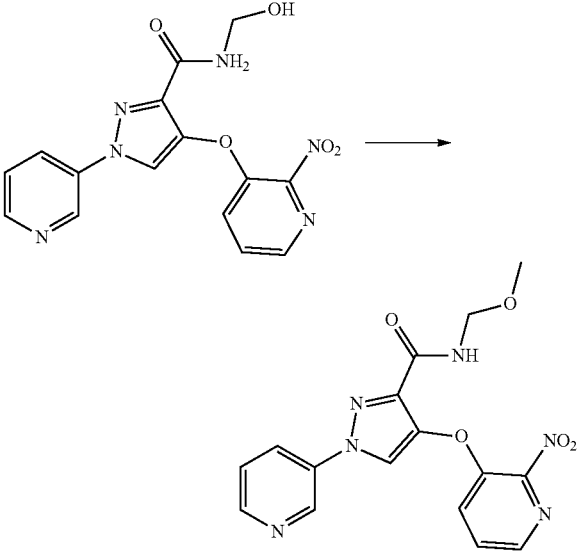

Oxalic acid (0.19 g, 2.07 mmol) was added to methanol (85 mL) solution of N-(hydroxymethyl)-4-((2-nitropyridin-3-yl)oxy)-1-(pyridin-3-yl)-1H-pyrazole-3-carboxamide (1.00 g, 2.80 mmol) until the pH of the solution reaches around 3, and stirred for 5 hours under heating to reflux. The reaction solution was returned to room temperature and then vacuum concentrated to obtain the title compound as a crude product.
Physical property: melting point 180° C.

Examples of products are shown below; it should be noted, however, that products are not limited to these examples. In Product Examples, "parts" refers to "parts by weight."

Product Example 1

| | |
|---|---|
| Compound according to the present invention | 10 parts |
| Xylene | 70 parts |
| N-methylpyrrolidone | 10 parts |
| Mixture of polyoxethylene nonyl phenyl ether and calcium alkyl benzene sulfonate | 10 parts |

The above ingredients were homogeneously mixed and dissolved, and made into an emulsion.

Product Example 2

| | |
|---|---|
| Compound according to the present invention | 3 parts |
| Clay powder | 82 parts |
| Diatomaceous earth powder | 15 parts |

The above ingredients were homogeneously mixed and crushed, and made into a powder.

Product Example 3

| | |
|---|---|
| Compound according to the present invention | 5 parts |
| Mixed powder of bentonite and clay | 90 parts |
| Calcium lignin sulfonate | 5 parts |

The above ingredients were homogeneously mixed and kneaded with an appropriate amount of water being added to it, after which the kneaded mixture was granulated and dried, and made into granules.

Product Example 4

| | |
|---|---|
| Compound according to the present invention | 20 parts |
| Kaolin and synthetic high-dispersion silicic acid | 75 parts |
| Mixture of polyoxethylene nonyl phenyl ether and calcium alkyl benzene sulfonate | 5 parts |

The above ingredients were homogeneously mixed and crushed, and made into a wettable powder.

Test Example 1

Test for control efficacy on Green Peach Aphid (*Myzus Persicae*)

Chinese cabbages were planted in plastic pots, each with a size of 8 cm in diameter and 8 cm in height, after which green peach aphids were propagated and the number of parasitic insects was examined in each pot. The compound or salt thereof expressed by General Formula (1) according to the present invention was dispersed in water and the dispersion was diluted to 500 ppm in the form of a reagent, after which the reagent was sprayed over stems and leaves of potted Chinese cabbages and let dry under wind, and the pots were kept in a greenhouse, and on the sixth day after the reagent was sprayed, the number of green peach aphids living parasitically on each Chinese cabbage was examined and the control efficacy was calculated based on the formula below, and judgement was made according to the criteria below.

$$\text{Preventive value} = 100 - \{(T/Ta)\lambda(Ca/C)\} \times 100 \quad \text{[Mathematical Formula 1]}$$

Ta: Number of parasitic insects inside the treatment area before spraying
T: Number of parasitic insects inside the treatment area after spraying
Ca: Number of parasitic insects inside the non-treatment area before spraying
C: Number of parasitic insects inside the non-treatment area after spraying
Criteria
A—control rate: 100%
B—control rate: 99% to 90%
C—control rate: 89% to 80%
D—control rate: 79% to 50%

Test Example 2. Test of Insecticidal Efficacy Against Small Brown Planthopper (*Laodelphax Striatellus*)

The compound or salt thereof expressed by General Formula (1) according to the present invention was dispersed in water and the dispersion was diluted to 50 ppm in the form of a reagent, after which rice plants raised from seeds (variety: Nipponbare) were soaked in the reagent for 30 seconds and dried under wind, and then placed in glass test tubes, each of which was inoculated with 10 third-instar larvae of small brown planthoppers and sealed with cotton, and eight days after the inoculation, the number of live insects and that of dead insects were examined and the corrected insect mortality was calculated based on the formula below, and judgement was made according to the criteria below.

$$\text{Corrected insect mortality}(\%) = \frac{\text{Survival rate in non-treatment area} - \text{Survival rate in treatment area}}{\text{Survival rate in non-treatment area}} \times 100 \quad \text{[Mathematical Formula 2]}$$

Criteria
A—Corrected insect mortality: 100%
B—Corrected insect mortality: 99% to 90%
C—Corrected insect mortality: 89% to 80%
D—Corrected insect mortality: 79% to 50%

Test Example 3. Test of Insecticidal Efficacy Against Whitefly (*Bemisia tabaci*)

The compound or salt thereof expressed by General Formula (1) according to the present invention was dispersed in water and the dispersion was diluted to 500 ppm in the form of a reagent, after which the diluent was sprayed over a tomato leaf obtained by cutting and then dried under wind. The leaf was fixed to a flask using an absorbent cotton so that a front surface of the leaf faces upward. Into this container, seven pairs of adult Whitefly were inoculated and then placed in a constant-temperature room with a temperature of 25° C. and a humidity of 65%, and insecticidal rate was calculated by examining survival or death of insects two days after inoculation, and judgement was made according to the criteria below. The test was repeated twice.

Criteria
A—Insecticidal rate: 100%
B—Insecticidal rate: 99% to 90%
C—Insecticidal rate: 89% to 80%
D—Insecticidal rate: 79% to 50%

The results show that, in Test Example 1, the compounds of Compound Nos. 1-1 and 1-2 among the compounds expressed by General Formula (1) according to the present invention have excellent insecticidal effects of judgement A against green peach aphids.

Additionally, in Test Example 2, the compounds of Compound Nos. 1-1 and 1-2 among the compounds expressed by General Formula (1) according to the present invention have insecticidal effects of judgement A against small brown planthopper.

Additionally, in Test Example 3, the compounds of Compound Nos. 1-1 and 1-2 among the compounds expressed by General Formula (1) according to the present invention have insecticidal effects of judgement A against Whitefly.

Test Example 4. Teratogenicity Test Using Zebrafish Embryo

Fertilized eggs obtained by mating zebrafish were cultured in a medium (0.3× Danieau's solution) at 28° C. until 6 hours after fertilization. Thereafter, the embryo was transferred to a medium into which the compound expressed by General Formula (1) according to the present invention dissolved in dimethyl sulfoxide was added, and cultured at 28° C. for five days. The concentration of dimethyl sulfoxide in the medium was 0.1%. 12 embryos were tested in each test concentration of the present invention. Five days after fertilization, survival or death of eggs and hatching conditions were determined under a stereoscopic microscope, and morphological abnormalities of the following sites and swimming behavior were observed for survivors.

Observation sites: notochord, tail, somite, eye, otolith, jaw, heart, blood vessel, abdomen, fin, etc.

From the results of these observations, the presence or absence of teratogenicity risk of the compound expressed by General Formula (1) according to the present invention and six compounds (Compound Nos. 4-10, 1-67, 1-1, 8-125, and 8-22, and a compound encompassed by the claims of Patent Literature 1 (Comparative Compound 4)) disclosed in the aforementioned Patent Literature 1 as the comparative compounds was determined.

The results are shown in Table 2 below.

It is noted that the teratogenicity test using zebrafish embryo is known to have good high predictivity to the teratogenicity test using the mammals (Reference Literature: Reproductive Toxicology 2012, (33), 155-164).

TABLE 2

| Compound No. | Structure | Teratogenicity risk |
|---|---|---|
| 1-1 | 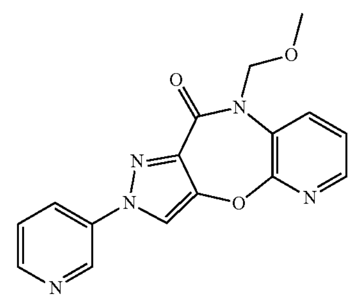 [SMILES: COCN1C(=O)c2nn(-c3cccnc3)cc2Oc2ncccc21] | No |
| Comparative Compound 1 (Compound No. 4-10 of Patent Literature 1). | 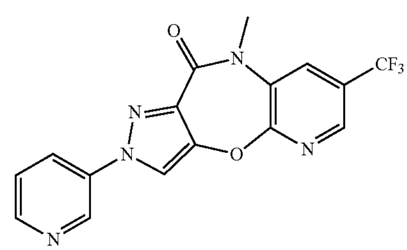 [SMILES: CN1C(=O)c2nn(-c3cccnc3)cc2Oc2ncc(C(F)(F)F)cc21] | Yes |
| Comparative Compound 2 (Compound No. 1-67 of Patent Literature 1) | 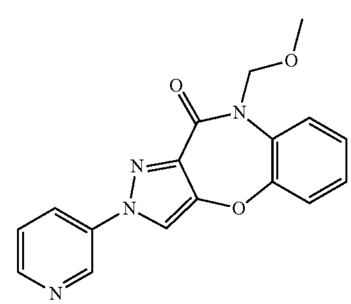 [SMILES: COCN1C(=O)c2nn(-c3cccnc3)cc2Oc2ccccc21] | Yes |

TABLE 2-continued

| Compound No. | Structure | Teratogenicity risk |
|---|---|---|
| Comparative Compound 3 (Compound No. 1-1 of Patent Literature 1) | 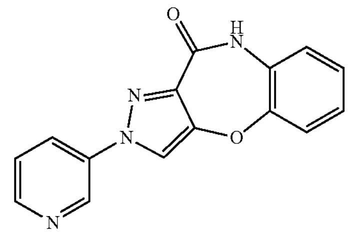 [SMILES: O=C1Nc2ccccc2Oc2cn(-c3cccnc3)nc21] | Yes |
| Comparative Compound 4 (Compound encompassed by the claims of Patent Literature 1) | 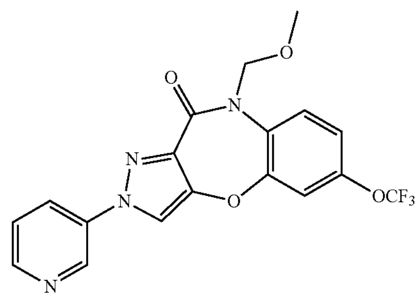 [SMILES: COCN1C(=O)c2nn(-c3cccnc3)cc2Oc2cc(OC(F)(F)F)ccc21] | Yes |
| Comparative Compound 5 (Compound No. 8-125 of Patent Literature 1) | 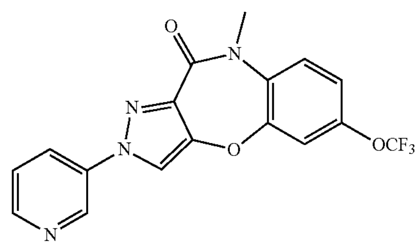 [SMILES: CN1C(=O)c2nn(-c3cccnc3)cc2Oc2cc(OC(F)(F)F)ccc21] | Yes |
| Comparative Compound 6 (Compound No. 8-22 of Patent Literature 1) | 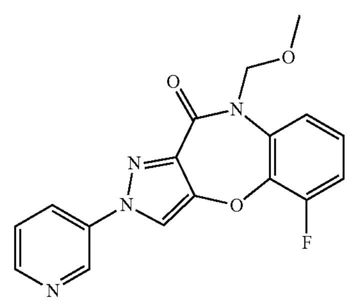 [SMILES: COCN1C(=O)c2nn(-c3cccnc3)cc2Oc2c(F)cccc21] | Yes |

As shown in Table 2, among the compound groups having the same basic backbone, the compound expressed by General Formula (1) according to the present invention was determined to have no teratogenicity risk in the teratogenicity test using zebrafish embryo.

Since the teratogenicity test using zebrafish embryo is a technology known to have high predictivity to the teratogenicity test using the mammals as described above, it was found from the aforementioned test results that the compound expressed by General Formula (1) according to the present invention is a compound group with reduced harmful effects to animals including humans.

INDUSTRIAL APPLICABILITY

The compound or salt thereof as proposed by the present invention is very useful in terms of having excellent effects as an agricultural/horticultural insecticide and reduced harmful effects to animals including humans.

The invention claimed is:

1. A compound, or a salt thereof, expressed by General Formula (1):

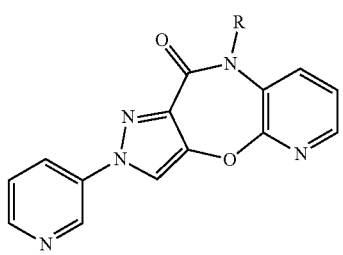

(1)

wherein R is a methoxymethyl group.

2. An agricultural and horticultural insecticide characterized by containing the compound or salt thereof according to claim 1 in an amount effective to manifest insecticidal efficiency.

3. A method for controlling agricultural and horticultural insect pests, comprising applying the agricultural and horticultural insecticide according to claim 2 to plants or soil by an effective amount.

* * * * *